United States Patent
Huang et al.

(10) Patent No.: US 12,247,224 B2
(45) Date of Patent: Mar. 11, 2025

(54) ORGANOIDS FOR DRUG SCREENING AND PERSONALIZED MEDICINE

(71) Applicant: SENTING, LLC, Chestnut Hill, MA (US)

(72) Inventors: Ling Huang, Toronto (CA); Senthil Muthuswamy, Toronto (CA)

(73) Assignees: Senthil Muthuswamy, Toronto (CA); Ling Huang, Toronto (CA)

(*) Notice: Subject to any disclaimer, the term of this patent is extended or adjusted under 35 U.S.C. 154(b) by 0 days.

(21) Appl. No.: 15/500,240

(22) PCT Filed: Jul. 30, 2015

(86) PCT No.: PCT/CA2015/050723
§ 371 (c)(1),
(2) Date: Jan. 30, 2017

(87) PCT Pub. No.: WO2016/015158
PCT Pub. Date: Feb. 4, 2016

(65) Prior Publication Data
US 2017/0267977 A1    Sep. 21, 2017

Related U.S. Application Data

(60) Provisional application No. 62/139,831, filed on Mar. 30, 2015, provisional application No. 62/030,999, filed on Jul. 30, 2014.

(51) Int. Cl.
| C12N 5/071 | (2010.01) |
| C12N 5/00 | (2006.01) |
| C12N 5/09 | (2010.01) |
| G01N 33/50 | (2006.01) |

(52) U.S. Cl.
CPC ......... *C12N 5/0678* (2013.01); *C12N 5/0062* (2013.01); *C12N 5/0676* (2013.01); *C12N 5/0693* (2013.01); *G01N 33/5011* (2013.01); *G01N 33/507* (2013.01); *G01N 33/5088* (2013.01); *C12N 2500/38* (2013.01); *C12N 2501/11* (2013.01); *C12N 2501/115* (2013.01); *C12N 2501/119* (2013.01); *C12N 2501/15* (2013.01); *C12N 2501/16* (2013.01); *C12N 2501/33* (2013.01); *C12N 2501/385* (2013.01); *C12N 2501/999* (2013.01); *C12N 2506/02* (2013.01); *C12N 2533/90* (2013.01)

(58) Field of Classification Search
None
See application file for complete search history.

(56) References Cited

U.S. PATENT DOCUMENTS

| 2014/0302491 A1* | 10/2014 | Nadauld | C12N 5/0688 |
| | | | 435/5 |
| 2015/0361393 A1* | 12/2015 | Nicholas | C12N 5/0618 |
| | | | 435/366 |

FOREIGN PATENT DOCUMENTS

| WO | WO 2012168930 | 12/2012 | |
| WO | WO-2012168930 A2 * | 12/2012 | ............. C12N 5/067 |

OTHER PUBLICATIONS

Kent, Kyle et al. Bovine pituitary extract provides remarkable protection against oxidative stress in human prostate epithelial cells. In Vitro Cell. Dev. Biol.-Animal 39:388-394, Sep. and Oct. 2003 (Year: 2003).*
Xue, Xiang et al. In vitro Organoid Culture of Primary Mouse Colon Tumors. Journal of V1SUalized Experiments (75). pp. 1-5. (Year: 2013).*
Agbunag et al., *Methods in Enzymology* 407 (2006) 703-710.
Anderson et al., *Appl. Immunohistochem Mol. Morphol.* 18:1 (2010) 3-8.
Beucken et al., *Nature Communications* 5:5203 (2014).
Boj et al., *Cell* 160 (2015) 324-338.
Chakravarty et al., *Cancer Biology & Therapy* 11:1 (2011) 71-83.
Chakravarty et al., *Experimental Biology and Medicine* 236 (2011) 145-155.
Chang et al., *Current Opinion in Genetics & Development* 24 (2014) 74-81.
Cheng et al., *Cell Stem Cell* 10:4 (2012) 371-384.
Dennis et al., *Clin. Cancer Res.* 11:10 (2005) 3766-3772.
Gao et al., *Cell* 159 (2014) 176-187.
Ghaneh et al., *Gut* 56 (2007) 1134-1152.
Hick et al., *BMC Developmental Biology* 9:66 (2009).
Huang et al., *Nature Medicine* 21:11 (2015) 1364-1371.
Huch et al., *The EMBO Journal* 32 (2013) 2708-2721.
International Preliminary Report on Patentability for PCT/CA2015/050723, mailed Jan. 31, 2017.
International Search Report and Written Opinion for PCT/CA2015/050723, mailed Oct. 21, 2015.
Jennings et al., *Diabetes* 62 (2013) 3514-3522.
Johnson et al., *Mutat. Res.* 640:1-2 (2008) 174-179.
Kanji et al., *CMAJ* 185.14 (2013) 1219-1226.
Kolodecik et al., *Frontiers in Physiology* 4:415 (2014).
Lagendijk et al., *J. Clin. Pathol.* 52 (1999) 283-290.
Laitio et al., *J. Anat.* 117.3 (1974) 619-634.
Li et al., *Nature Medicine* 20.7 (2014) 769-777.
Lyttle et al., *Diabetologia* 51 (2008) 1169-1180.
Marusyk et al., *Nature Reviews: Cancer* 12 (2012) 323-334.
Mccracken et al., *Seminars in Cell & Developmental Biology* 23 (2012) 656-662.

(Continued)

*Primary Examiner* — Nghi V Nguyen
(74) *Attorney, Agent, or Firm* — Robert C. Netter, Jr.; Dann, Dorfman, Herrell & Skillman

(57) ABSTRACT

Cell culture mediums for generating organoids, including tumour organoids. Specifically, such mediums comprise: a cell culture medium; an antioxidant; a serum free supplement; an insulin receptor agonist; a glucocorticoid; and an FGFR agonist. Other aspects involve methods of generating tumour organoids from tumours. Such methods can comprise generating pancreatic progenitor organoids from pluripotent stem cells, pancreatic lineage committed progenitors.

18 Claims, 16 Drawing Sheets

(56) References Cited

OTHER PUBLICATIONS

Nielsen et al., *Developmental Dynamics* 237 (2008) 2039-2052.
Outzen et al., *Transplantation* 32.2 (1981) 101-105.
Pagliuca et al., *Cell* 159 (2014) 428-439.
Pan et al., *Developmental Dynamics* 240 (2011) 530-565.
Rezania et al., *Nature Biotechnology* 32.11 (2014) 1121-1133.
Riedel et al., *Diabetologia* 55 (2012) 372-381.
Sato et al., *Cell* 161 (2015) 1700.
Schiesser et al., *Ann. N.Y. Acad. Sci.* 1311 (2014) 124-137.
Shamir et al., *Nature Reviews: Molecular Cell Biology* 15 (2014) 647-664.
Viale et al., *Nature* 514:7524 (2014) 628-632.
Vincent et al., *Lancet* 378 (2011) 607-620.
Waddell et al., *Nature* 518:7540 (2015) 495-501.
Xiang et al., *Methods in Enzymology* 406 (2006) 692-701.
Xue et al., *Journal of Visualized Experiments* 75 (2013) e50210.
Brunner et al., "Serum-free cell culture: the serum-free media interactive online database." *Altex*, 27(1): 53-62, 2010.

* cited by examiner

ORGANOIDS FOR DRUG SCREENING AND PERSONALIZED MEDICINE

RELATED APPLICATIONS

This application is a national phase application under 35 U.S.C. § 371 of International Application No. PCT/CA2015/050723 filed Jul. 30, 2015, which claims priority to U.S. Provisional Application Nos. 62/030,999 and 62/139,831 filed on Jul. 30, 2014 and Mar. 30, 2015, respectively. The entire contents of each of the above-referenced disclosures is specifically incorporated by reference herein without disclaimer.

TECHNICAL FIELD

This disclosure relates generally to methods to generate and maintain organoids and cell culture mediums for same.

BACKGROUND

Pancreatic cancer is one of the deadliest malignancies. Late presentation and high mortality highlight a desperate need for early detection methods and new treatment strategies. More than 95% of pancreatic cancers originate from the exocrine compartment, comprised of acinar and ductal cells. Around 90% of exocrine tumors are ductal adenocarcinoma, which accounts for most of the mortality[1,2]. Cellular origins of human pancreatic ductal adenocarcinoma (PDAC) are poorly understood. Genetically, dysregulation of KRAS, p16$^{INK4A}$/CDKN2A, TP53, and SMAD4/DPC4 are the most frequent events associated with initiation and progression of PDAC[3]. Neither the biological changes associated with precancerous lesions (such as pancreatic intraepithelial neoplasia (PanIN)) nor their progression to PDAC are well understood. Progenitors from mouse pancreas grown in organoid cultures have been used to investigate normal ductal morphogenesis and to model early disease[4-6]. However, there is a lack of culture models for understanding the mechanisms by which PDAC is initiated and progresses in human cells.

Several studies have shown that human pluripotent stem cells (PSCs) can be committed towards the pancreatic lineage, in particular towards the endocrine lineage to generate insulin-producing beta-cells[7-9]. To our knowledge it has not been possible to enable the differentiation of PSCs towards exocrine lineage to generate ductal and acinar cells. In addition to modeling normal development in culture, there is a significant demand to grow primary human PDAC as organoids for understanding cancer biology and for developing and validating new therapeutic options.

While it is important to understand cancer biology in normal cells, such as pancreatic cells, it is also of critical importance in developing, and validating therapeutic options, particularly in testing personalized therapeutic options, to be able to grow and test patient derived tumour cells.

Tumor diversity represents one of the major challenges for cancer drug development (Tentler et al. 2012). Particularly with the emergence of specific, targeted cancer therapies, it has become more important to identify tumor subpopulations which respond to anti-cancer therapy. To date, this testing has required patient-derived xenograft (PDX) models, which require grafting of patient derived tumour cells onto immune compromised mice. While PDX models have been shown generally retain the histological characteristics of the parental patient tumors, and can be generated from a wide range of cancer types and reflect the heterogeneity within and in between different cancer histotypes (Fiebig et al. 1999, Fiebig et al. 2001; Uronis et al. 2012; Guerreschi et al. 2013; Jin et al. 2010), they have the disadvantage of taking signficant time to generate. Therefore there is demand for other options to study patient derived tumour cells.

SUMMARY

In an aspect, there is provided. In an aspect, there is provided a medium for growing cells comprising: a cell culture medium; an antioxidant; a serum free supplement; an insulin receptor agonist; a glucocorticoid; and an FGFR agonist.

In an aspect, there is provided a use of the medium for growing cells as described herein for generating tumour organoids from tumours.

In an aspect, there is provided a use of the medium for growing cells as described herein for generating pancreatic progenitor organoids from pluripotent stem cells, pancreatic lineage committed progenitors In an aspect, there is provided a method for generating tumour organoids from tumours, optionally comprising primary tumour cells, comprising: digesting the tumour isolated from a sample; resuspending the tumour cells in the medium for growing cells described herein, preferably along with a biomatrix substance; plating the tumour cells, optionally on a same or different biomatrix substance.

In an aspect, there is provided a medium for maintaining cells, preferably, pancreatic progenitor organoids cells, comprising: a cell culture medium; an antioxidant; and a serum free supplement. In some embodiments, the cell culture medium; antioxidant; and serum free supplement are, and present at concentration of, those described above with respect to the medium for growing cells.

In an aspect, there is provided a method for generating pancreatic progenitor organoids from pluripotent stem cells, pancreatic lineage committed progenitors, comprising: digesting the pancreatic progenitors isolated from a sample; resuspending the progenitors in the medium for growing cells described herein, preferably along with a biomatrix substance; plating the tumour cells, optionally on a same or different biomatrix substance; and replacing the medium with the medium for maintaining cells described herein.

In an aspect, there is provided a tumour organoid generated by the methods described herein.

In an aspect, there is provided a pancreatic progenitor organoid generated by the methods described herein.

In an aspect, there is provided a use of the organoids described herein for drug screening, drug discovery or drug response.

BRIEF DESCRIPTION OF THE DRAWINGS

In the drawings, embodiments are illustrated by way of example. It is to be expressly understood that the description and drawings are only for the purpose of illustration and as an aid to understanding, and are not intended as a definition of the limits of the invention.

Embodiments will now be described, by way of example only, with reference to the attached figures, wherein.

DETAILED DESCRIPTION

Figure 1:
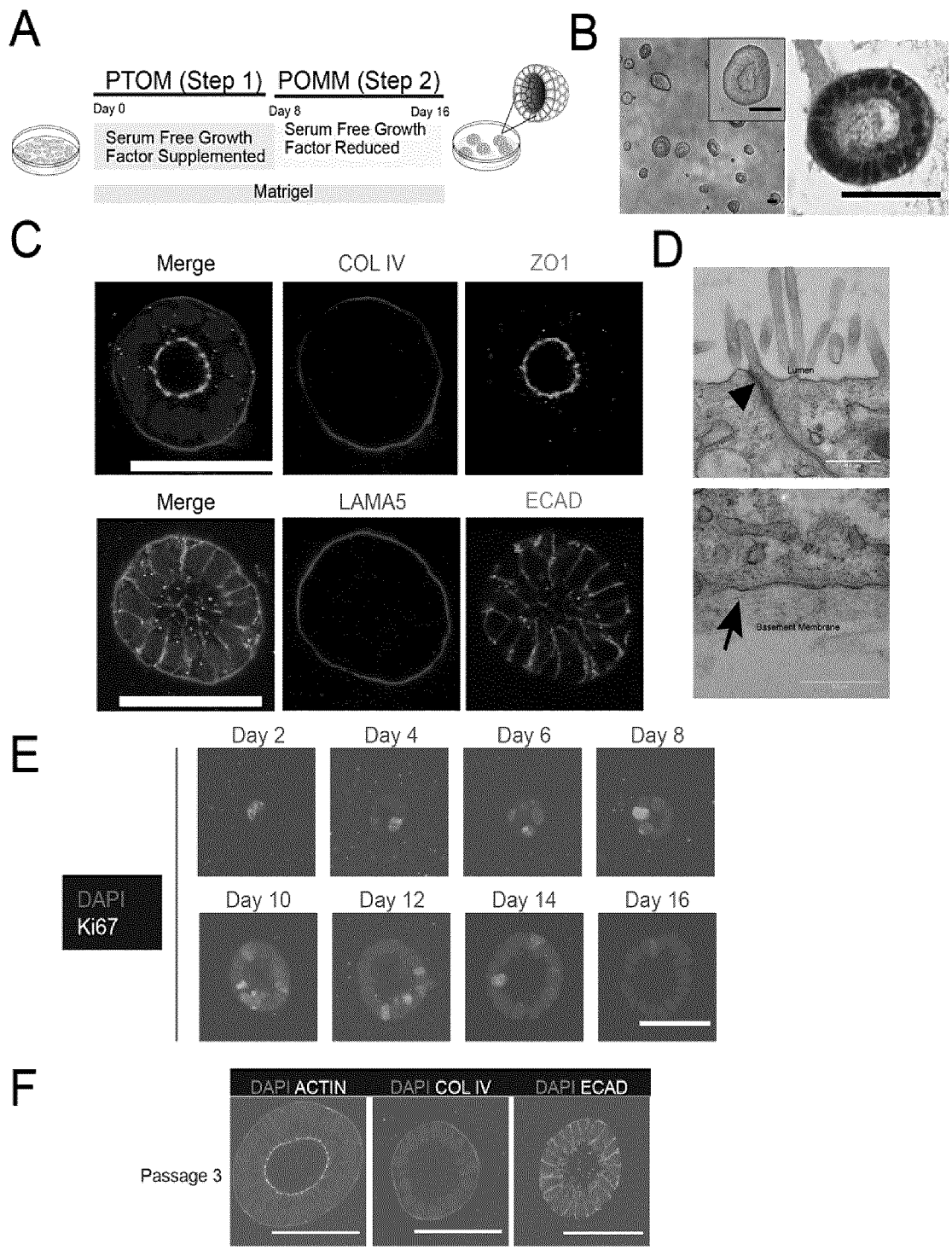
FIG. 1 shows Induction of Polarized Organoids from Pluripotent Human Stem Cells. (A) A schematic diagram of the two-step differentiation protocol for growing pancreatic lineage committed pluripotent stem cells (PSCs) on a 3D Matrigel. PTOM refers to Pancreatic Progenitor and Tumor-organoid Media and POMM refers to Pancreatic Organoid Maintenance Media. (B) Phase morphology of day 16 organoids (left panel) with insert representing high magnification image of one typical organoid. H&E staining of one typical organoid (right panel). (C) Confocal images of day 16 organoids immunostained for basal polarity markers (COLLAGEN IV (COLIV) or LAMININ α5 (LAMA5), tight junction marker (ZO1), cell-cell junction marker, E-CADHERIN (ECAD). (D) Transmission electron micrograph of cells from day 16 3D organoids. Upper panel shows apical region of epithelia, arrowhead pointing to an electron dense region representing tight junctions. Lower panel, shows basal region of polarized epithelia with the arrowhead pointing to basement membrane. Scale bars, 0.5 µm. (E) Expression of cell proliferation marker Ki67 at different days in 3D culture. (F) Maintenance of polarity upon serial passaging of organoids as shown ACTIN, COLLAGEN IV (COL IV) and E-CADHERIN (ECAD). Scale bars represent 50 µm, unless specified otherwise.

In the following description, numerous specific details are set forth to provide a thorough understanding of the invention. However, it is understood that the invention may be practiced without these specific details.

There is a dearth of in vitro models for exocrine pancreas development and primary human pancreatic adenocarcinoma (PDAC). We define three-dimensional culture conditions to induce differentiation of human pluripotent stem cells (PSCs) into exocrine progenitor-organoids that form ductal and acinar structures in culture and in vivo. Expression of mutant KRAS or TP53 in progenitor-organoids induces mutation-specific phenotypes in culture and in vivo. TP53R175H expression induced cytosolic SOX9 localization in organoids. In patient tumors, cytosolic SOX9 significantly correlated with TP53 mutation and disease-specific mortality. In addition, we define culture conditions for clonal generation of tumor-organoids from freshly resected PDAC.

Tumor-organoids maintain the differentiation status and reproduce the histoarchitecture observed in primary tumors. Furthermore, tumor-organoids retain patient-specific traits such as hypoxia, oxygen consumption, repressive epigenetic marks, and differential sensitivity to EZH2 inhibition. Thus, progenitor-organoids and tumor-organoids can be effective tools for modeling PDAC and for identifying precision therapy strategies.

In an aspect, there is provided a medium for growing cells comprising: a cell culture medium; an antioxidant; a serum free supplement; an insulin receptor agonist; a glucocorticoid; and an FGFR agonist.

An organoid is cell/tissue culture forming an (at least) three-dimensional organ-bud, which typically mimics, at least partially, organ structure and/or function. The organoids described herein are preferably spheroid and are not adhered to a plate.

In some embodiments, the medium for growing cells further comprises an antibiotic, preferably Pen-strep, Neomycin, Bleomycin, or Ampicillin. Preferably, the antibiotic in the medium is at a concentration of 25-250 u/ml, preferably 50-100 u/ml.

The cell culture medium may be any growth or culture medium suitable for growing and/or maintaining the desried cell type. Similarity, appropriate serum free supplements for the particular cell type would be known to a person skilled in the art. Cell culture mediums and serum free supplements are described in Mitry and Hughes, *Human Cell Culture Protocols, Third Edition*, Springer Protocols, Humana Press (2012) and Freshney, *Culture of Animal Cells: A Manual of Basic Technique and Specialized Applications*, John Wiley & Sons, (2011).

In some embodiments, the cell culture medium is DMEM, F12, L-15, or RPMI; preferably DMEM.

In some embodiments, the antioxidant is vitamin A or its derivatives, Resveratrol, Fisetin, or L-Glutathione, preferably vitamin A.

In some embodiments, the serum free supplement is bovine pituitary extract (BPE), B27, N2, or NS21.

In some embodiments, the insulin receptor agonist is insulin, Demethylasterriquinone B1, HNG6A, IGF1, or IGF2; preferably insulin.

In some embodiments, the glucocorticoid is Dexamethasone, Fluticasone propionate, Hydrocortisone, or Corticosterone; preferably Hydrocortisone.

In some embodiments, the FGFR agonist is at least one of FGF1, FGF2, FGF3, FGF4, FGF5, FGF6, FGF7, FGF8, FGF9 and FGF10, or any combinations thereof. For example, two or more FGFR agaonists may be used together, for example, FGF1 and FGF9; FGF7 and FGF9; FGF2 and FGF10; FGF2 and FGF7; FGF1 and FGF7; FGF3 and FGF 5; FGF4 and FGF8; FGF2, FGF7 and FGF9; FGF2 and FGF9.

In some embodiments, the medium for growing cells further comprises a retinoic receptor agonist, preferably retinoic acid.

In some embodiments, the antioxidant in the medium is at a concentration of 1-200 ug/ml, preferably 25-75 ug/ml.

In some embodiments, the serum free supplement in the medium is at a concentration of 0.1-10%, preferably 0.5-2% by volume.

In some embodiments, the insulin receptor agonist in the medium is at a concentration of 1-50 ug/ml, preferably 5-25 ug/ml.

In some embodiments, the glucocorticoid in the medium is at a concentration of 0.1-2.5 ug/ml, preferably 0.25-1 ug/ml.

In some embodiments, the FGFR in the medium is at a concentration of 1-200 ng/ml, preferably 2.5-100 ng/ml.

In some embodiments, the medium for growing cells further comprises an EGFR agonist. Preferably, the EGFR agonist is EGF, HGF, a TGF, a NRG, or Amphiregulin. In some embodiments, the EGFR agonist in the medium is at a concentration of 1-200 ng/ml, preferably 1-50 ng/ml.

In an aspect, there is provided a use of the medium for growing cells as described herein for generating tumour organoids from tumours.

As used herein, a "tumour" is a swelling of a part of the body, generally without inflammation, caused by an abnormal growth of tissue, whether benign or malignant. In certain embodiments, the tumour is solid. Independently, is some embodiments, the tumour is malignant. Tumour organoids that can be generated using the media and methods described herein may include tumours associated with adrenal cancer, anal cancer, bile duct cancer, bladder cancer, bone cancer, brain/cns cancer, brain/cns cancer, breast cancer, cervical cancer, colon/rectum cancer, endometrial cancer, esophagus cancer, eye cancer, gallbladder cancer, gastrointestinal cancer, kidney cancer, laryngeal and hypopharyngeal cancer, liver cancer, lung cancer, malignant mesothelioma, nasal cavity and paranasal sinus cancer, nasopharyngeal cancer, neuroblastoma, oral cavity and oropharyngeal cancer, ovarian cancer, pancreatic cancer, penile cancer, pituitary tumors, prostate cancer, retinoblastoma, salivary gland cancer, sarcoma, skin cancer, small intestine cancer, stomach cancer, testicular cancer, thymus cancer, thyroid cancer, uterine sarcoma, vaginal cancer, vulvar cancer, or wilms tumor.

Preferably, the tumour is a pancreatic tumour, a lung tumour, a prostate tumour, a colon tumour, a breast tumour, a liver tumour, a renal cell tumour or a brain tumour. EGF is preferably used when generating lung organoids.

The tumour organoids typically take about 16 days to be estabilshed. In some embodiments, the tumour organoids are stable for up to 1 year in the medium, preferably 2-8 weeks.

In an aspect, there is provided a use of the medium for growing cells as described herein for generating pancreatic progenitor organoids from pluripotent stem cells, pancreatic lineage committed progenitors In some embodiments, the use further comprises use of a second medium for maintaining cells comprising: a cell culture medium; an antioxidant; and a serum free supplement. In an aspect, there is provided a method for generating tumour organoids from tumours, optionally comprising primary tumour cells, comprising: digesting the tumour isolated from a sample; resuspending the tumour cells in the medium for growing cells described herein, preferably along with a biomatrix substance; plating the tumour cells, optionally on a same or different biomatrix substance. The biomatrix substance may be any substance such as Matrigel™ or Cultured BME™ which may be added to media to simulate the extracellular environment within an organism. The biomatrix substance is typically proteinaceous (e.g. collagen, laminin) and along with the medium can form a semisolid or gel-like environment. It is also known to use egg white in this manner.

In an aspect, there is provided a medium for maintaining cells, preferably, pancreatic progenitor organoids cells, comprising: a cell culture medium; an antioxidant; and a serum free supplement. In some embodiments, the cell culture medium; antioxidant; and serum free supplement are, and present at concentration of, those described above with respect to the medium for growing cells.

In an aspect, there is provided a method for generating pancreatic progenitor organoids from pluripotent stem cells, pancreatic lineage committed progenitors, comprising: digesting the pancreatic progenitors isolated from a sample; resuspending the progenitors in the medium for growing cells described herein, preferably along with a biomatrix substance; plating the tumour cells, optionally on a same or different biomatrix substance; and replacing the medium with the medium for maintaining cells described herein.

Organoids are preferably incubated in the medium for growing cells as described herein for at least 4 days, and may be kept in the same for up to 9 months, preferably 1-6 weeks before being transferred to the medium for maintaining cells described herein.

In an aspect, there is provided a tumour organoid generated by the methods described herein.

In an aspect, there is provided a pancreatic progenitor organoid generated by the methods described herein.

In an aspect, there is provided a use of the organoids described herein for drug screening, drug discovery or drug response.

The advantages of the present invention are further illustrated by the following examples. The examples and their particular details set forth herein are presented for illustration only and should not be construed as a limitation on the claims of the present invention.

EXAMPLES

Materials and Methods

Three Dimensional Culture of Organoids

Human embryonic stem cell (hESC)-derived pancreatic progenitors were generated in a monolayer format using a modification of our previously described staged differentiation protocol[1,2]. Stem cells were regularly tested to be mycoplasma free. To generate definitive endoderm, hESCs (MEL1 cell line) on MEFs were induced with 100 ng/ml ActivinA (R&D Systems) and 1 uM CHIR 99021 for 1 day in RPMI supplemented with 2 mM glutamine (Gibco-BRL) and $4.5 \times 10^{-4}$ M MTG (Sigma), then with 100 ng/ml ActivinA and 1 uM CHIR 99021 and 2.5 ng/ml bFGF (R&D Systems) for 1 day in RPMI supplemented with glutamine, 0.5 mM ascorbic acid (Sigma), and MTG. The media was then changed to 100 ng/ml ActivinA and 2.5 ng/ml bFGF for an additional day in RPMI supplemented with glutamine, ascorbic acid, and MTG. The day three endoderm population was next patterned for two days by culture in the presence of 50 ng/ml FGF10 and 250 nM KAAD-cyclopamine (Toronto Research Chemicals, ON, Canada) in RPMI supplemented with glutamine, MTG and 1% vol/vol B27 supplement (Invitrogen). At this stage, pancreatic progenitors were induced with 50 ng/ml noggin, 50 ng/ml FGF10, 250 nM cyclopamine, 2 uM retinoic acid, and 50 ng/ml exendin4 for two days in DMEM supplemented with glutamine, ascorbic acid and B27. Following induction, the population was cultured in the presence of 50 ng/ml noggin, 50 ng/ml EGF, 1.2 ug/ml Nicotinamide, and 50 ng/ml exendin4 DMEM supplemented with glutamine, ascorbic acid and B27 to promote the development of PDX-1+ NKX6.1+ progenitors (Stem Cell Reports. 2015 Apr. 14; 4(4):591-604) Cells were harvested at day nine of differentiation for generation of ductal/acinar structures.

For pancreas progenitor organoid culture, T9 cells were resuspended and plated in the PTOM (Pancreatic Progenitor and Tumor Organoid Media) containing DMEM with factors including serum-free supplements, FGFs, and insulin. The cells were plated on a bed of Matrigel as described before 3. At day 8 in 3D culture, replace culture medium with fresh POMM (Pancreatic Organoid Maintenance Media) (PTOM media without FGFs) with 5% Matrigel every 4 days. PODM I (Pancreatic Organoid Differentiation Media) contains DMEM with B27, 2-phospho ascorbic acid, FGF, EGF, TGF beta inhibitors. PODM II contains DMEM with B27, 2-phospho ascorbic acid, FGF, EGF. Fresh tissues of primary tumors from patients were washed twice with DMEM, digested with collagenase (Roche) and resuspended in PTOM. Tumor cells were then seeded in 3D culture chambers as described above. Culture media were replaced every 4 days. For serial passaging of organoids, day 16 organoids were treated with collagenase for 2 hours then further dissociated with trypsin for 10-30 minutes. Cells were collected and re-seeded in 3D culture following protocols as described above. MCF-10A cells were obtained from ATCC. Gene expression data will be uploaded into NCBI's Gene Expression Omnibus (GEO).

For gene transduction, KrasG12V, p53R175H and turboRFP were cloned into a pSicoR vector with EF1apha promoter (Addgene, 31847) using Gateway system (Life Technologies). Lentiviruses were packaged using a third generation packaging system and peusdotyped with RabiesG (Addgene, 15785) in 293T cells. Concentrated virus was used to infect pluripotent progenitors grown on a thin layer of Matrigel in PTOM and subsequently replated in 3D, as outlined above.

Preferred PTOM and POMM components are set forth below.

PTOM

| Component | Concentrations Ranges | Preferred Concentrations |
|---|---|---|
| Cell Culture Medium (such as DMEM, F12, L-15, RPMI) | | |
| Antibiotics (eg., Pen-Strep, Neomycin, Bleomycin, Ampicillin) | 25-250 u/ml | 50-100 u/ml |
| Antioxidant (eg., Vitamin A derivatives, Resveratrol, Fisetin, L-Glutathione) | 1-200 ug/ml | 25-75 ug/ml |
| Serum-free supplements (eg., B27, N2, NS21) | 0.1-10% | 0.5-2% |
| Insulin Receptor Agonists (eg, Insulin, Demethylasterriquinone B1, HNG6A, IGF1, IGF2) | 1-50 ug/ml | 5-25 ug/ml |
| Glucorticoid (eg., Dexamethasone, Fluticasone propionate, Hydrocortisone, Corticosterone) | 0.1-2.5 ug/ml | 0.25-1 ug/ml |
| FGFR agonists (eg., FGFs) | 1-200 ng/ml | 2.5-100 ng/ml |
| EGFR agonists (eg., EGF, HB-EGF, TGFs, NRGs, BTC, Amphiregulin, Epiregulin) | 1-200 ng/ml | 1-50 ng/ml |

POMM

| Component | Concentrations Ranges | Preferred Concentrations |
|---|---|---|
| Cell Culture Medium (such as DMEM, F12, L-15, RPMI) | | |
| Antibiotics (eg., Pen-Strep, Neomycin, Bleomycin, Ampicillin) | 25-250 u/ml | 50-100 u/ml |
| Antioxidant (eg., Vitamin A derivatives, Resveratrol, Fisetin, L-Glutathione) | 1-200 ug/ml | 25-75 ug/ml |
| Serum-free supplements (eg., B27, N2, NS21) | 0.1-10% | 0.5-2% |

| Reagents | Function |
|---|---|
| Antibiotics (eg., Pen-Strep) | Reduce cutlure contamination |
| Antioxidant (eg., Vitamin A derivatives) | Help cell survival |
| Serum-free supplements (eg., B27) | Cell survival |
| Insulin Receptor Agonists (eg, Insulin) | Increase cell proliferation |
| Glucorticoid (eg., Hydrocortisone) | Increase cell proliferation |
| FGFR agonists | Maintain cell differentiation and morphogenesis |

Brightfield and Fluorescent Imaging 3D cultured cells in chamber slides were fixed with 4% PFA and processed as in 3D culture of MCF10A cells[32]. Tissues and histogel blocks were fixed in 10% Formalin and paraffin blocks were processed using standard immununohistochemistry protocol. Phase contrast images were acquired on a Nikon TE300 microscope with 4× or 10× objective and a DS-F12 camera. Confocal images were acquired with the Olympus FluoView 1000 system. Images were acquired with a 20× air objective or a 40× oil objective with 1024×1024 resolution. See extended experimental procedures for detailed image analysis.

Gene Expression Analysis

Adult pancreas RNAs were purchased from Clontech. Fetal tissue RNAs were purchased from Biochain (www.Biochain.com). RNAs of 3D cultured organoids or cells lines were obtained using Trizol. Global gene expression analysis was performed using Illumina Human HT-12 v4 Expression BeadChip array and analyzed with R (for details of bioinformatics analysis, see extended experimental procedures). cDNAs were synthesized using Superscript III First Strand Synthesis Supermix for RT-PCR (Thermo). Student's t-tests were performed to determine the statistical significances of gene expression differences between different conditions. The primers for PCR are listed in supplemental documents.

Results and Discussion
Induction of Polarized Organoids from Pluripotent Human Stem Cells Ductal/acinar (exocrine) lineage develops from NKX6.1+ PDX1+ progenitors in vivo[10]. A PSC-derived, pancreatic lineage committed, population that contained NKX6.1+ PDX1+ cells (FIG. 8) was plated in three-dimensional (3D) cell culture and screened for growth factors and nutrient supplements (see Methods section) that are known to be critical for pancreas development[11,12]. A combination of factors including FGFs, insulin and B27 serum-free supplements induced 10-20% of PSC-derived cells to form polarized 3D structures (FIG. 1A and see Method section for details). Those that did not form structures died during the process.

The 3D structures were mostly clonally derived, as determined by serial imaging analysis (FIG. 8B). They were comprised of a single layer of polarized epithelial cells surrounding a hollow central lumen (FIG. 1B, 1C). In addition, the epithelial cells secreted their basement membrane as determined using human-specific antibodies recognizing Collagen IV and Laminin α5 (FIG. 1C). Tight junctions, basement membrane and apical microvilli were also detected by transmission electron microscopy (FIG. 1D). Karyotyping analysis confirmed that the cells in 3D structures had a normal diploid genome (FIG. 8C).

Cell proliferation and organ size control are important features associated with normal tissue morphogenesis. The progenitor-organoids underwent significant increase in size and were highly proliferative from day 0 to day 12, (FIG. 1E, FIG. 8D, 8E). By day 14, over 95% of organoids were proliferation-arrested with a diameter ranging between 30-200 micrometers (FIG. 8D, 8E).

Figure 8:
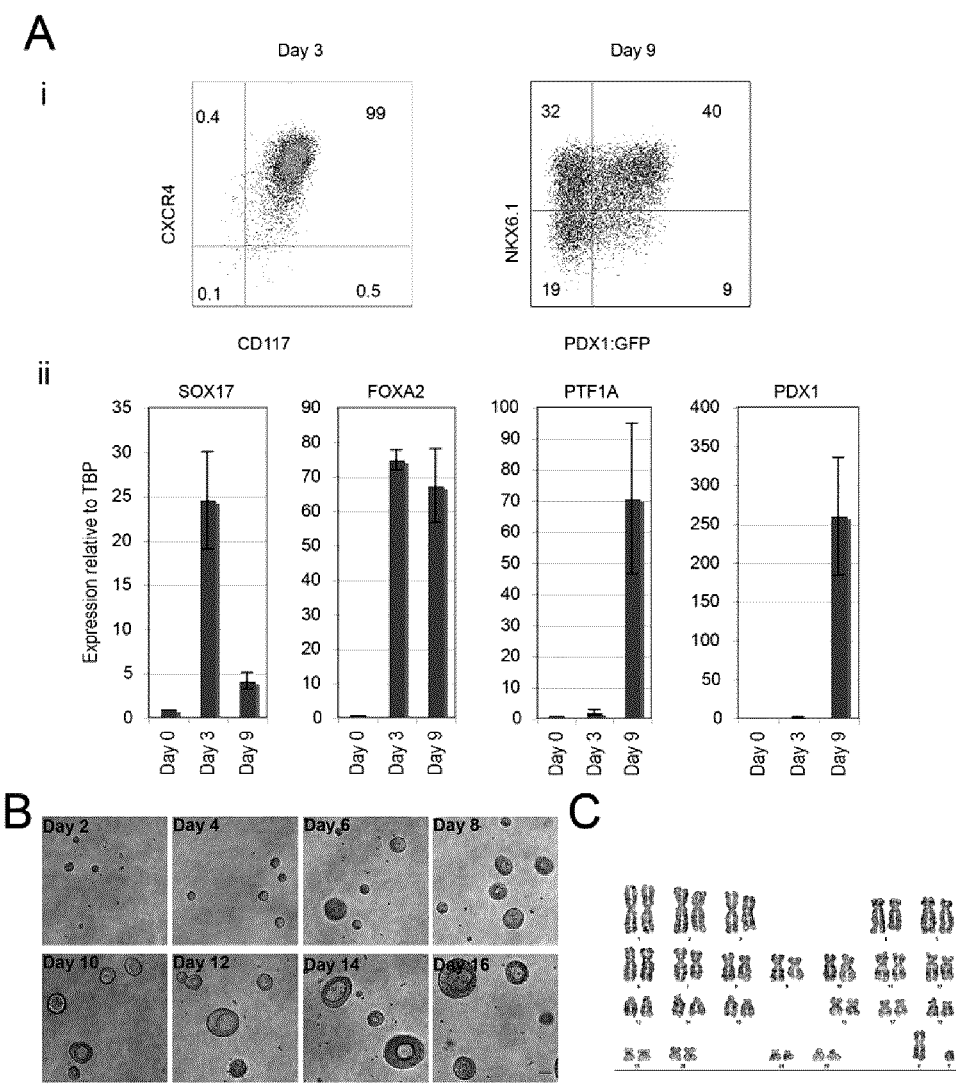
FIG. 8 shows Differentiation and Morphogenesis of Polarized Organoids from Induced Progenitors. (A) Induction of pancreatic lineage cells. i) Flow cytometric validation of efficient definitive endoderm induction from MEL1-derived PDX1-GFP hESC by co-expression of CXCR4 and CD117 (T3, left panel). Flow cytometric analysis of PDX1-GFP and NKX6.1 expression in day 9 multipotent pancreatic progenitors (T9, right panel). ii) Real time PCR analysis for SOX17, FOXA2, PTF1A and PDX1 expression in hESCs (TO), definitive endoderm (T3), and multipotent pancreatic progenitors (T9, day 0 for 3D culture), (n=3, data represent mean+/−S.E.M). (B) Time sequence of organoid morphogenesis. Images were taken every 2 days with a phase contrast microscope. Scale bar, 50 µm. (C) Karyotype of cells in Day 16 Pancreatic Progenitor Organoids. All metaphase cells karyotyped (5/5) showed 46 chromosomes with normal diploid male human karyotype. (D) Quantification of Ki67 positive organoids during 3D morphogenesis. An organoid was counted as proliferative when more than 5% of cells in the organoid were positive for Ki67 staining. Graph summarizes results from three independent sets of experiments with over 100 structures counted in each experiment. (E) Changes in organoid size during morphogenesis as depicted in areas (left chart). Data are presented as box plots. The box represents the interquartile range between first and third quartile and the median value represented by a solid line. The whiskers, 5% and 95% percentiles of the measurements; box top, third quartiles of measurements; box bottom, first quartile of the measurements; center line, median measurements. (F) Quantification of apoptotic organoids at different days in 3D culture. An organoid was counted as apoptotic when at least one apoptotic cell was present. Graph summarizes results from three independent sets of experiments with over 100 structures counted in each experiment. (G) Morphology of organoids from passage 2 and passage 3 as observed by a phase contrast microscope. Scale bar, 50 µm.
Figure 8:
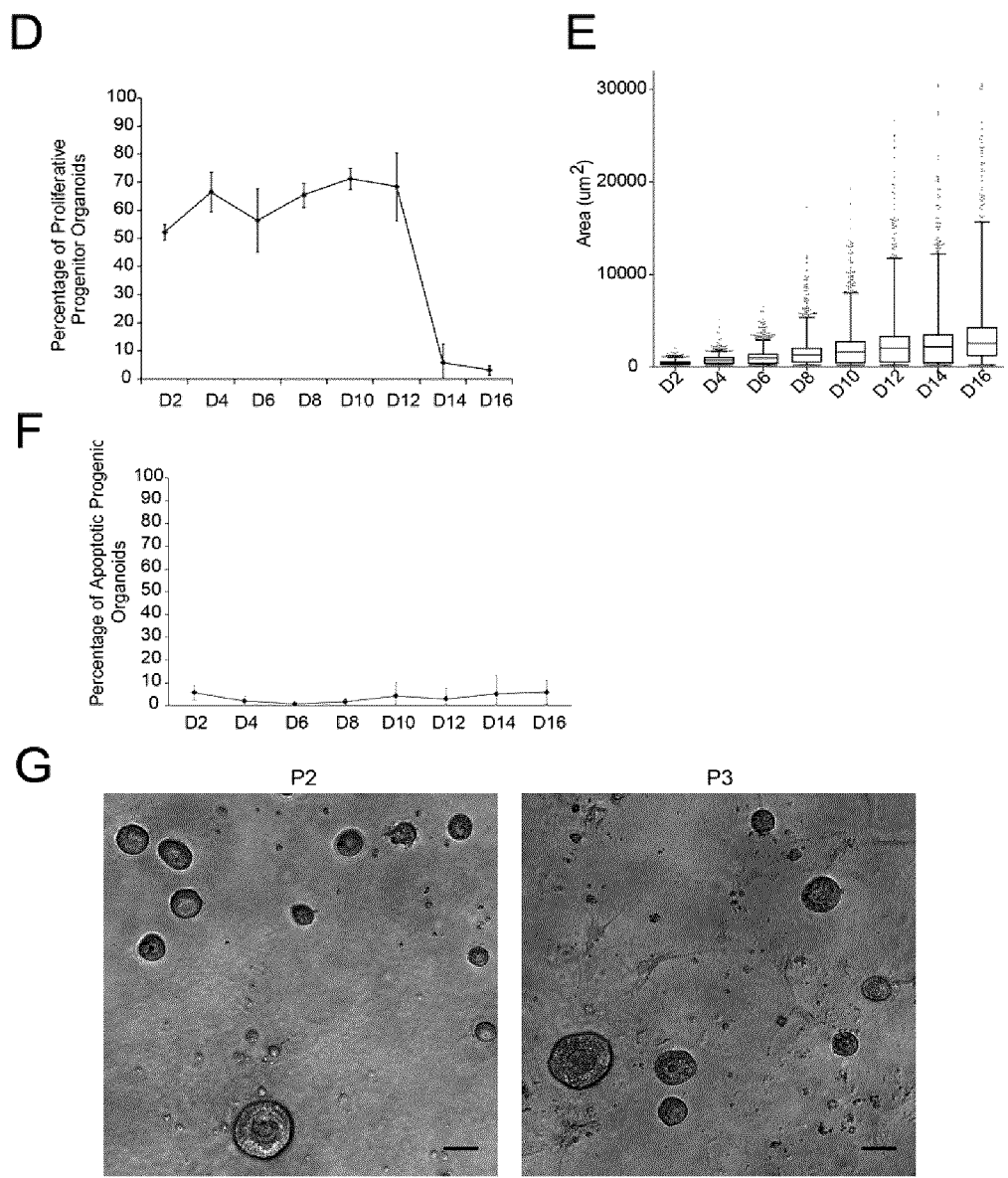

We rarely detected the apoptotic cell marker, cleaved caspase-3, in the organoids (FIG. 8), demonstrating that the hollow lumen formation does not involve cell death. This is consistent with the finding that apoptosis is not required during lumen formation of embryonic pancreatic ducts in vivo[13]. Apical-basal polarity was established starting day 8, as monitored using apical membrane markers, MUC1, and ZO-1 and the basal surface marker, Collagen IV (data not shown). The day 16 organoids can be serially passaged (tested up to passage 5) to re-initiate organogenesis (FIG. 8G). The resulting organoids still maintained size control, had hollow lumens and established apical-basal polarity (FIG. 1F).

Organoids Express Markers Associated with Pancreatic Progenitor Cells

Figure 2:
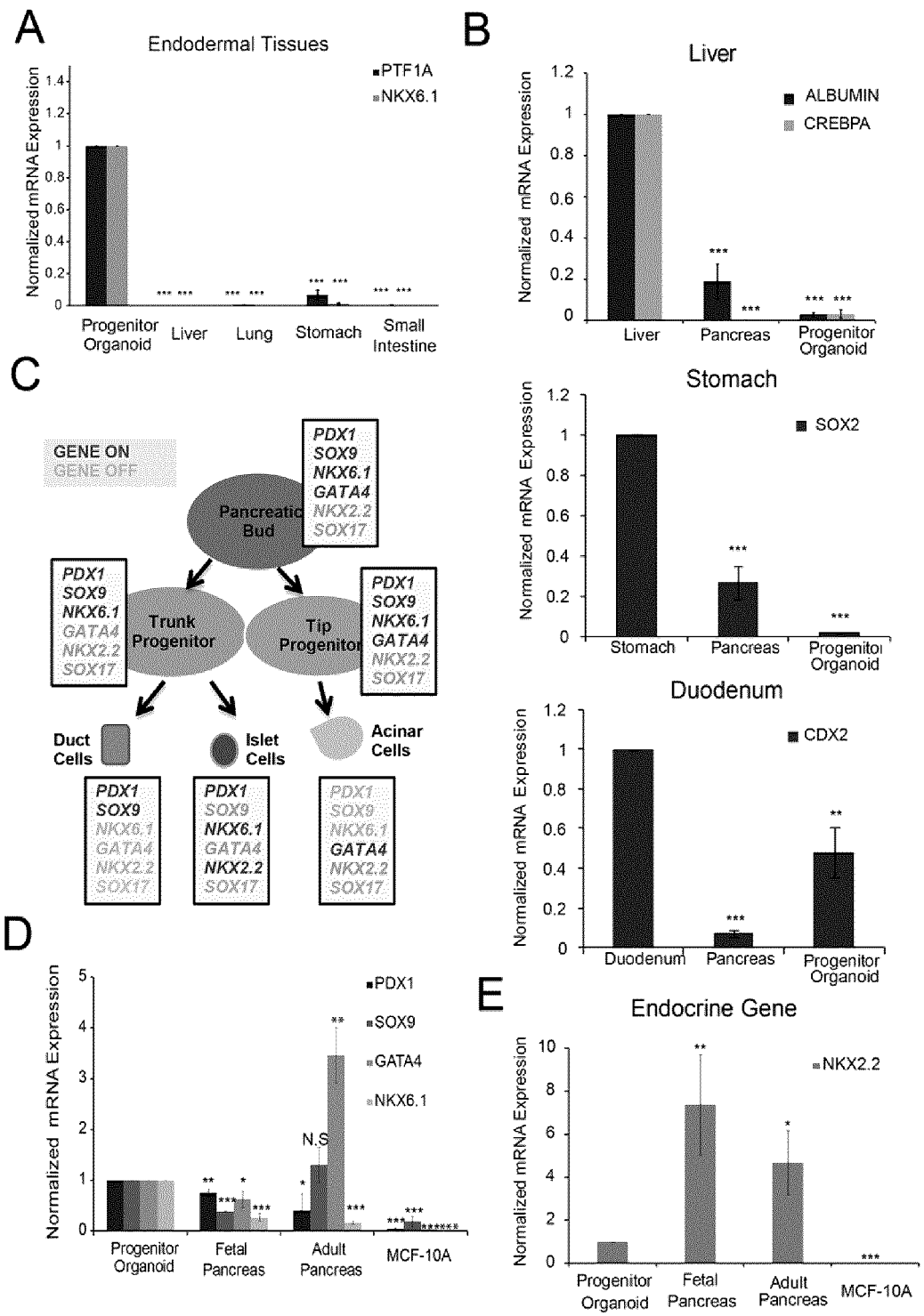
FIG. 2 shows that Organoids Express Markers Associated with Pancreatic Progenitor Cells. (A) Expression of pancreas exocrine specific marker genes in 3D organoids and human fetal endodermal tissues. (B) Expression of markers for liver (albumin, CREBPA), stomach (SOX2) and duodenum (CDX2) in 3D organoids, human fetal pancreas and positive control (fetal liver or fetal stomach or fetal duodenum). (C) A schematic summary of expression patterns of transcription factors during human embryonic pancreas development. Expressed genes are in dark; repressed genes are in grey, adapted from Jennings et al10. (D) Expression of pancreas markers in 3D organoids, MCF-10A mammary epithelial cells used as non-specific control. (E) Expression of NKX2.2, a pancreatic endocrine marker gene. (F) Expression of markers associated with differentiated ductal, acinar or islet cells. CA2, carbonic anhydrase II; CFTR, cystic fibrosis transmembrane conductance regulator; CEL, carboxyl ester lipase; PNLIP, pancreatic lipase; SPINK1, serine peptidase inhibitor 1. For all qPCR experiments data represent mean+/− S.E.M. P value (t-test, two tailed): N.S.—not significant; *-p=0.01-0.05; -p=0.001-0.01; *, p=<0.001 (n=3).
Figure 2:
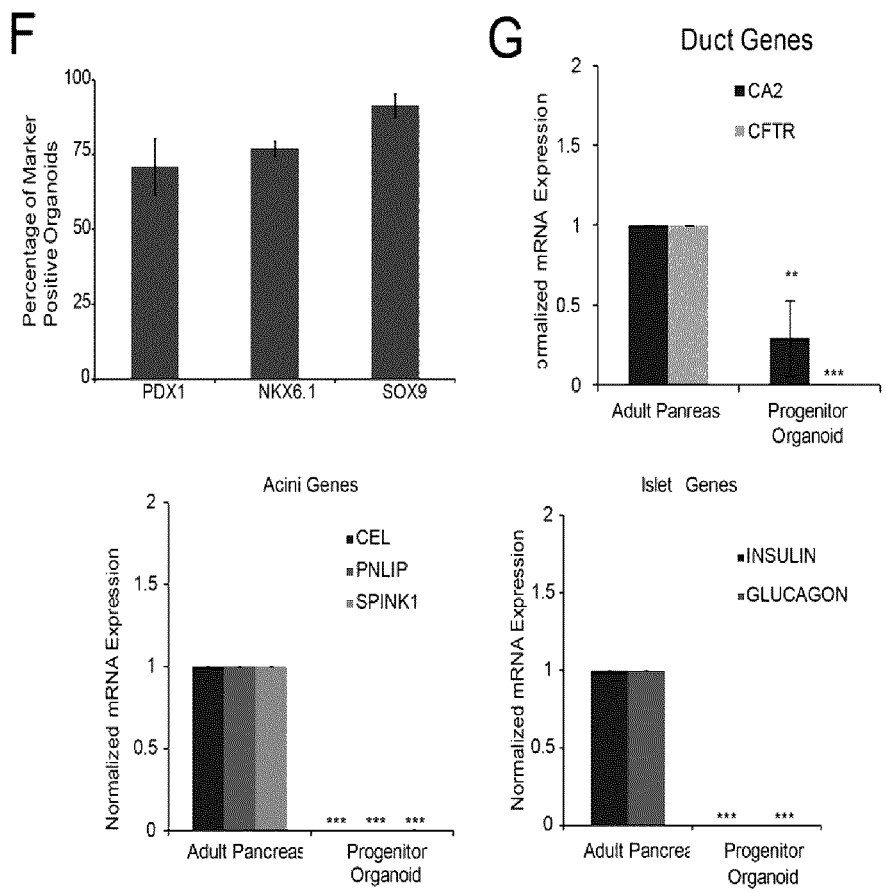
Figure 9:
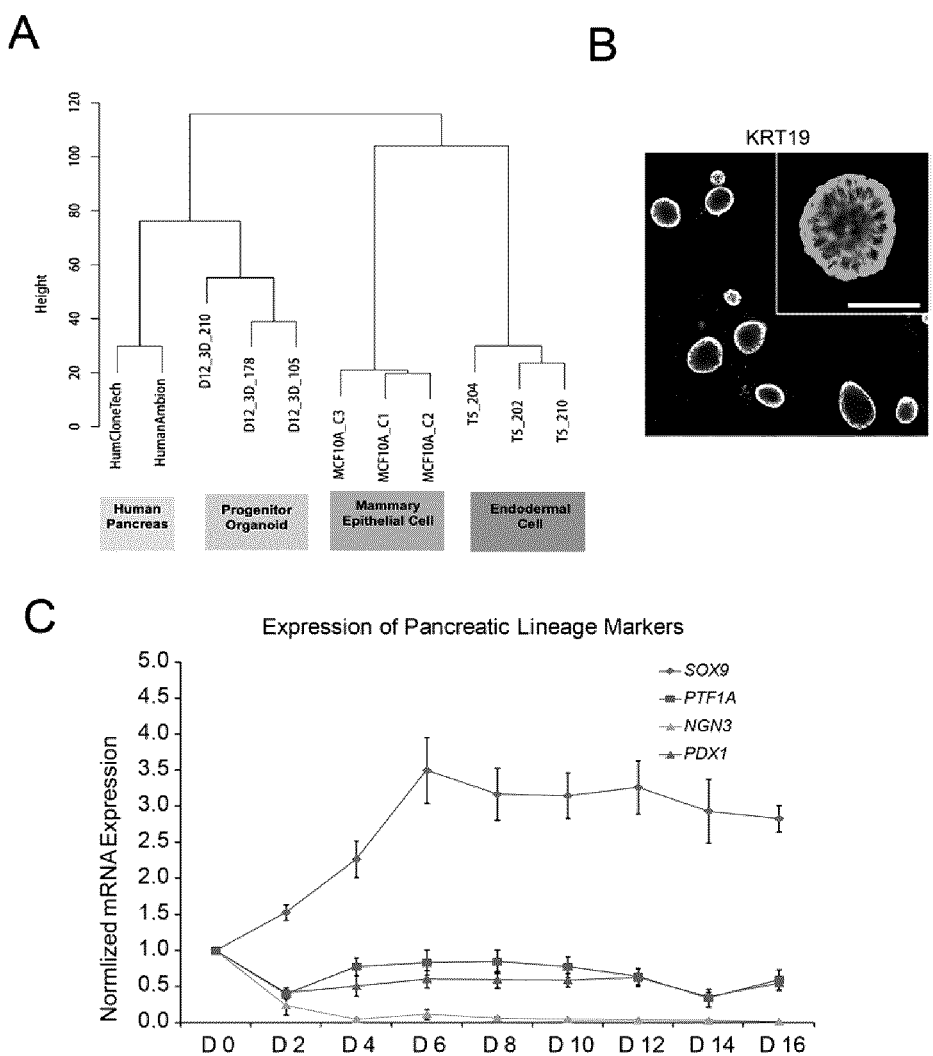
FIG. 9 shows Formation 3D Organoids by Pancreatic Exocrine Epithelial Cells. (A) Global gene expression in progenitor organoids. Gene expressions in pancreatic progenitor organoids, human adult pancreas, mammary epithelial cells line MCF-10A and definitive endoderm cells were detected by Illumina HT12 V4 Expression BeadChip. Dendrogram showed unsupervised clustering of pancreatic progenitor organoids close to human adult pancreas. (B) Expression of cytokeratin 19 (KRT19) in pancreatic progenitor organoid. All progenitor-organoids expressed pancreatic ductal epithelial cytokeratin KRT19. Insert, high resolution image of one organoid. Scale bar, 50 µm. (C) Expression of markers associated with progenitor cells during 3D morphogenesis. The chart summarizes experiments from three independent experiments (data represent mean+/− S.E.M).

Global gene expression analysis and unsupervised clustering placed 3D organoids close to human pancreas compared to endodermal cells or a human mammary epithelial cell line (MCF-10A) (FIG. 9A). In addition, expression of NKX6.1 and PTF1A, transcription factors highly expressed in the pancreas compared to other endoderm-derived organs, were significantly higher in 3D structures compared to multiple endoderm-derived organs analyzed (FIG. 2A). By contrast, expression of liver-specific markers, albumin and CREBPA, and stomach and duodenum-specific markers, SOX2 and CDX2, were significantly lower in both human pancreas tissue and in 3D structures compared to levels in liver, stomach and duodenum, respectively (FIG. 2B).

Next, we monitored expression of transcription factors that are expressed in a cell type-specific manner within the pancreas (FIG. 2C)[10,14,15]. In 3D structures, progenitor markers PDX1 and NKX6.1 were expressed at higher levels and the islet cell marker, NKX2.2, was expressed at a lower level compared to fetal and adult pancreas (FIGS. 2D and 2E). The expression of the acinar marker, GATA4, was higher in adult pancreas compared to fetal pancreas or the 3D structures (FIG. 2D). To understand the expression of these markers at single cell level, we analyzed protein expression by immunofluorescence. PDX1, SOX9 and NKX6.1 proteins were expressed in majority of 3D organoids (FIG. 2F). Expression of PDX1 protein was heterogeneous within each organoid (FIG. 2F). In addition, all structures and all cells within a structure, expressed Cytokeratin 19 (KRT19), a pancreatic epithelia associated cytokeratin (FIG. 9B).

The morphogenesis conditions promoted exocrine lineage specification as determined by a 3.5 fold increase SOX9 expression beginning on day 6 (FIG. 9C). Conversely, the conditions suppressed commitment towards endocrine lineage, as monitored by suppression of NGN3, an endocrine progenitor marker (FIG. 9C). Expression levels of PDX1 and PTF1A, pancreatic progenitor markers, remained constant from day two.

Next we examined if the organoids express markers associated with differentiated acinar, ductal or islet cells. Expression of Carbonic Anhydrase II (CA2), and CFTR (ductal cell markers), CEL, PNLIP and SPINK (acinar cell markers) or insulin and glucagon (islet cell markers) were either undetectable or significantly lower (CA2) in 3D structures compared to levels observed in adult pancreas (FIG. 2G), suggesting that the 3D structures were not terminally differentiated and consisted largely of progenitor cells. Henceforth, we refer to these 3D structures as progenitor-organoids.

Differentiation of Pancreatic Progenitor-Organoids In Vitro and In Vivo

Figure 3:
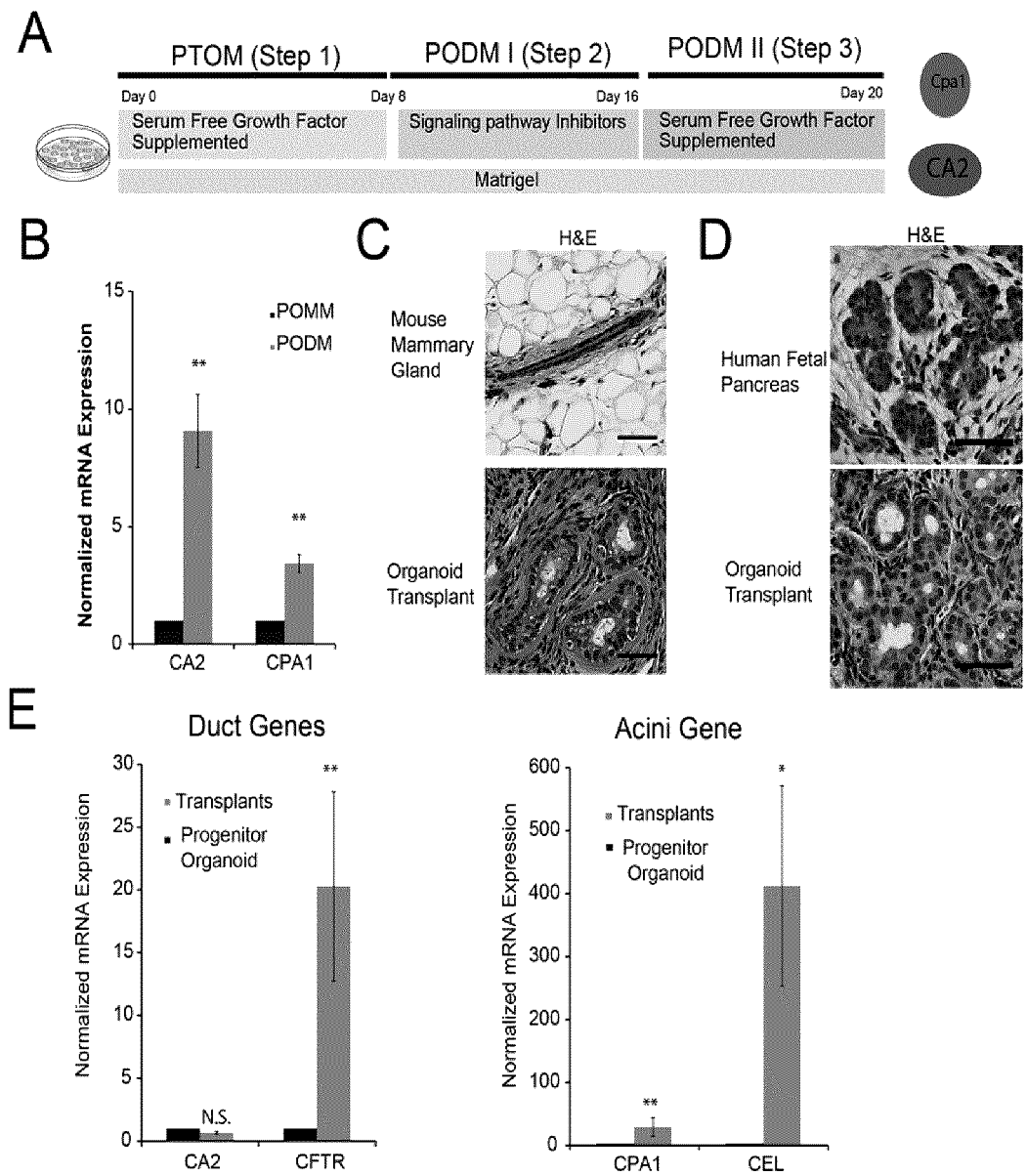
FIG. 3 shows Differentiation of Pancreatic Progenitor-organoids In Vitro and In Vivo. (A) Schematic representation of the three-step differentiation protocol used to induce differentiation of progenitor-organoids into ductal and acinar cells in culture. PTOM refers to Pancreatic Progenitor and Tumor-organoid Media; PODM1 refers to Pancreatic Organoid Differentiation Media and PODM2 refers to Pancreatic Organoid Differentiation Media 2. (B) QPCR analysis for ductal (CA2) and acinar (CPA1) markers grown as per protocol in panel A. (C) Top panel, H&E morphology of mammary ductal structures of control glands. Bottom panel represents glands transplanted with cells from progenitor-organoids stained with H&E (left panel). (D) Comparative analysis of organization of H&E stained human fetal pancreas (top panel) with transplanted outgrowths (bottom panel) (E) Quantitative PCR analysis showing expression of human acinar (CPA1, CEL) and ductal (CA2, CFTR) markers relative to the progenitor-organoids in transplanted outgrowths.

Next we investigated methods to induce differentiation of progenitor-organoids. Wnt, Notch, TGFβ and Hedgehog pathways have been implicated in normal pancreas development[11,12]. We used small molecule inhibitors of these pathways in various combinations to induce differentiation of progenitor-organoids. The protocol (FIG. 1A) was modified to include two additional steps, where step 2 involves inhibition of TGFβRI (A8301) and Notch (DBZ) (PODM I media) and step 3 has defined growth factors (PODM II) (FIG. 3A). This modified protocol induced differentiation of progenitor-organoids towards ductal (CA2+, 10-15%) or acinar (CPA1+, 0.5-1%) lineage (FIG. 3B and data not shown). The differentiated organoids showed significant increases in acinar and ductal marker mRNA expression compared to organoids in progenitor media (FIG. 3B).

We also tested if in vivo conditions would induce molecular and morphological differentiation of progenitor-organoids into pancreatic exocrine structures. We used mouse mammary gland fat pad as the site for in vivo growth as they were previously shown to support growth of pancreas islet cells[16]. Day 16 organoids were dissociated and injected into mammary gland fat pad of female NOD/SCID mice (6-8 weeks old), following animal user protocol approved by the Animal Care Committee at University Health Network. Fifteen weeks after injection >90% (20/22) of the glands had outgrowths that were morphologically distinct from the endogenous mammary ductal structures (FIG. 3C and data not shown). The outgrowths were analyzed for Human Leukocyte Antigen I (HLA I), to distinguish transplanted cells from mouse mammary cells (data not shown). We compared the organization of epithelial structures in transplants to human fetal pancreas tissue sections (FIG. 3D)[10,17]. In fetal pancreas, and in transplanted outgrowths, carboxypeptidase A (CPA1) positive acinar cell clusters were located close to KRT19 positive ductal structures (data not shown), demonstrating that progenitor-organoids can undergo organogenesis in vivo.

Quantitative PCR analysis further demonstrated increased expression of human acinar (CPA1, CEL) and ductal (CFTR) markers relative to the progenitor-organoids while CA2 expression did not change (FIG. 3E). We also observed that the organoid-derived structures lacked expression of NKX6.1 and maintain SOX9 expression in vivo as expected[10] (data not shown). Differentiated pancreatic ducts or islets, but not acini, are known to have primary cilia[18]. In organoid transplants, primary cilia were observed in ducts expressing CA2 but were absent in acinar like structures positive for CPA1 (data not shown). Thus, the progenitor-organoids can generate outgrowths that have molecular and morphological characteristics of human fetal exocrine pancreas.

Progenitor-Organoids for Modeling Disease In Vitro and In Vivo

Figure 4:
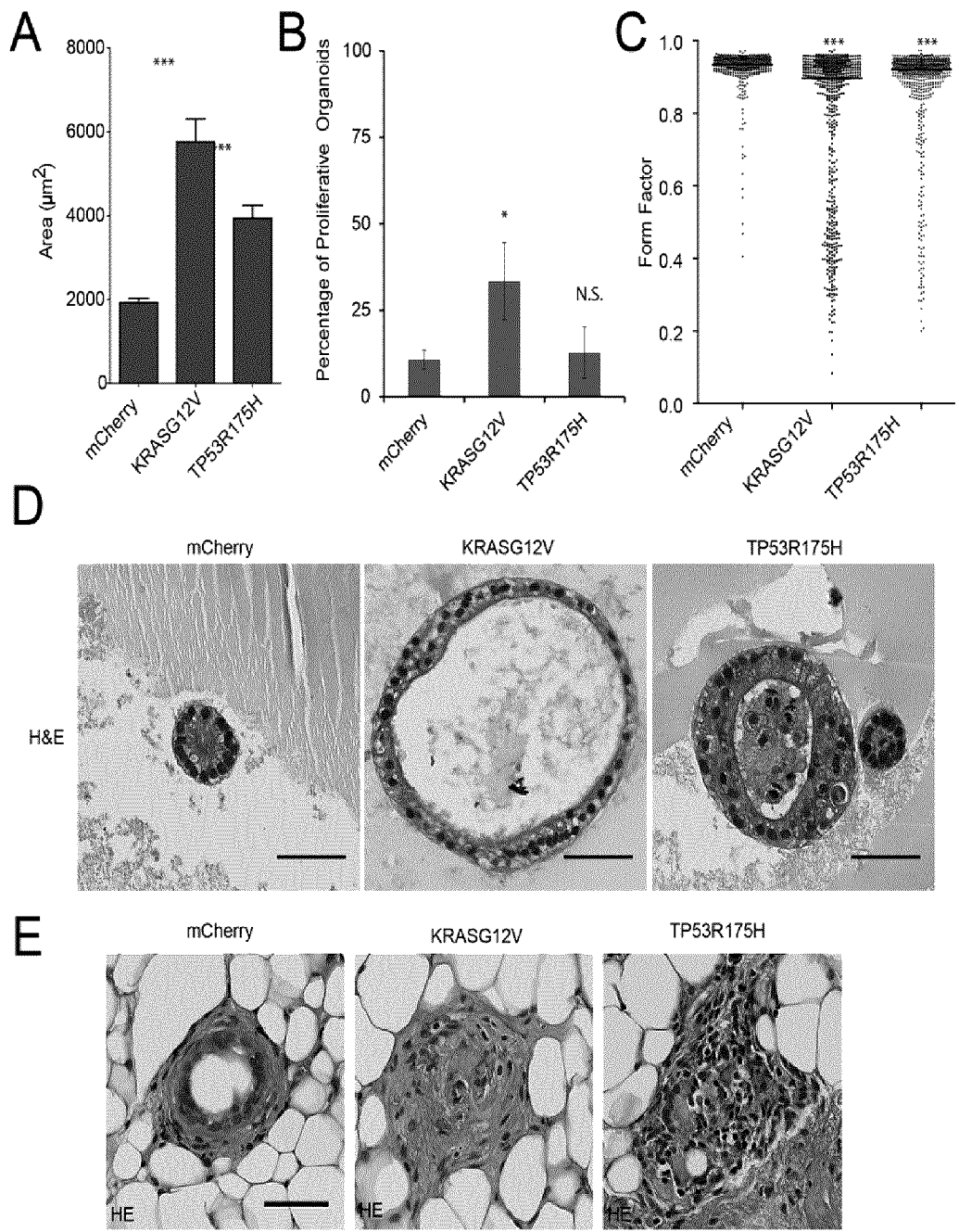
FIG. 4 shows Progenitors-organoids for Modeling Early Disease. (A) KRASG12V or TP53R175H infected progenitor-organoids are significantly larger than control mCherry expressing progenitor-organoids. (B) Quantification of the percentage of proliferative organoids. (C) Form factor (FF) analysis, a continuous scale where a perfect circle is represented by FF=1 and a linear line by FF=0. (D) H&E Images of mCherry, KRAS G12V and TP53R175H expressing structures stained with H&E. All quantification graphs summarize three independent experiments with n>100 structures assessed in all cases, N.S-, not significant; *-p=0.01-0.05; -p=0.001-0.01; *, p=<0.001 (n=3). (F) Transplant outgrowths from progenitor-organoids expressing mCherry, KRASG12V or TP53R175H. All scale bars represent 50 µm.
Figure 10:
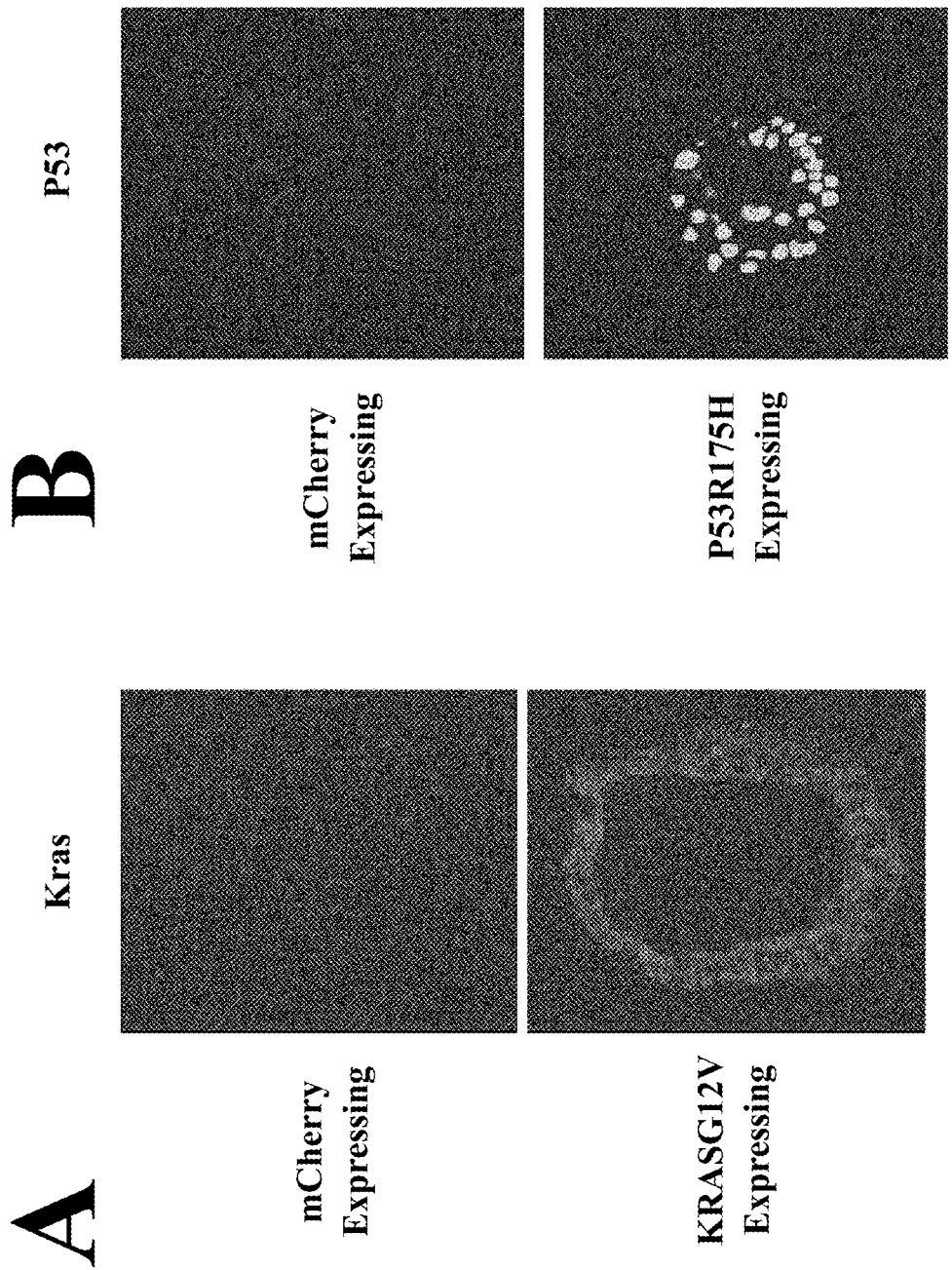
FIG. 10 shows Expression of KRAS and TP53 in Progenitor-organoids. (A) Expression of KRAS in progenitor-organoids. (B) Expression of P53 in progenitor-organoids. Scale bars, 50 µm.

We reasoned that progenitor-organoids can serve as a platform for modeling phenotypes associated KRAS and TP53 alterations; two of the most frequently observed events in PDAC[19,20]. Pancreatic lineage committed cells were infected with mCherry (control), KRASG12V or dominant negative mutant TP53, R175H. Organoids from KRASG12V and TP53R175H infected cells expressed detectable levels of the transgene (FIGS. 10A and 10B) and were significantly larger than mCherry expressing organoids (FIG. 4A). Although both KRASG12V and TP53R175H expressing structures had more cells per structure, TP53R175H expressing cells reached low proliferation rates by day16, whereas KRASG12V expressing organoids maintained high proliferation rates (FIG. 4B). Both KRASG12V and TP53R175H organoids were also disorganized compared to mCherry, as determined by form factor analysis (FIG. 4C).

Mutations in KRAS and CDKN2A, but not TP53 or SMAD4, are associated with PanIN1 lesions in humans, whereas, mutations in TP53 and SMAD4 are associated with PanIN3 lesions[1]. Interestingly, KRASG12V expressing organoids had a cystic organization with apically positioned nuclei, a morphology consistent with early pancreatic tumor lesions (FIG. 4D), whereas, TP53R175H expressing organoids had an atypical organization with apically positioned nuclei and filled lumens (FIG. 4D), demonstrating the ability of this model to generate genotype-specific phenotypes.

At day 16 the organoids were collected and injected into 8-10 mammary fatpads of NOD/SCID mice. The transplants were incubated for 5-6 months and mice were sacrificed for analysis. In the structures that grew, we confirmed their human origin of structures by staining for HLA and transgene expression (FIG. 4E and data not shown). Structures generated from mCherry expressing cells showed normal ductal organization, whereas outgrowths that expressed KRASG12V or TP53R175H showed abnormal ductal architecture and nuclear morphology consistent with neoplastic transformation. Thus, both in culture and in vivo, progenitor-organoids can serve as models for investigating early stages of transformation.

Cytoplasmic SOX9 and Its Relationship to TP53 Status and Clinical Outcome

Figure 5:
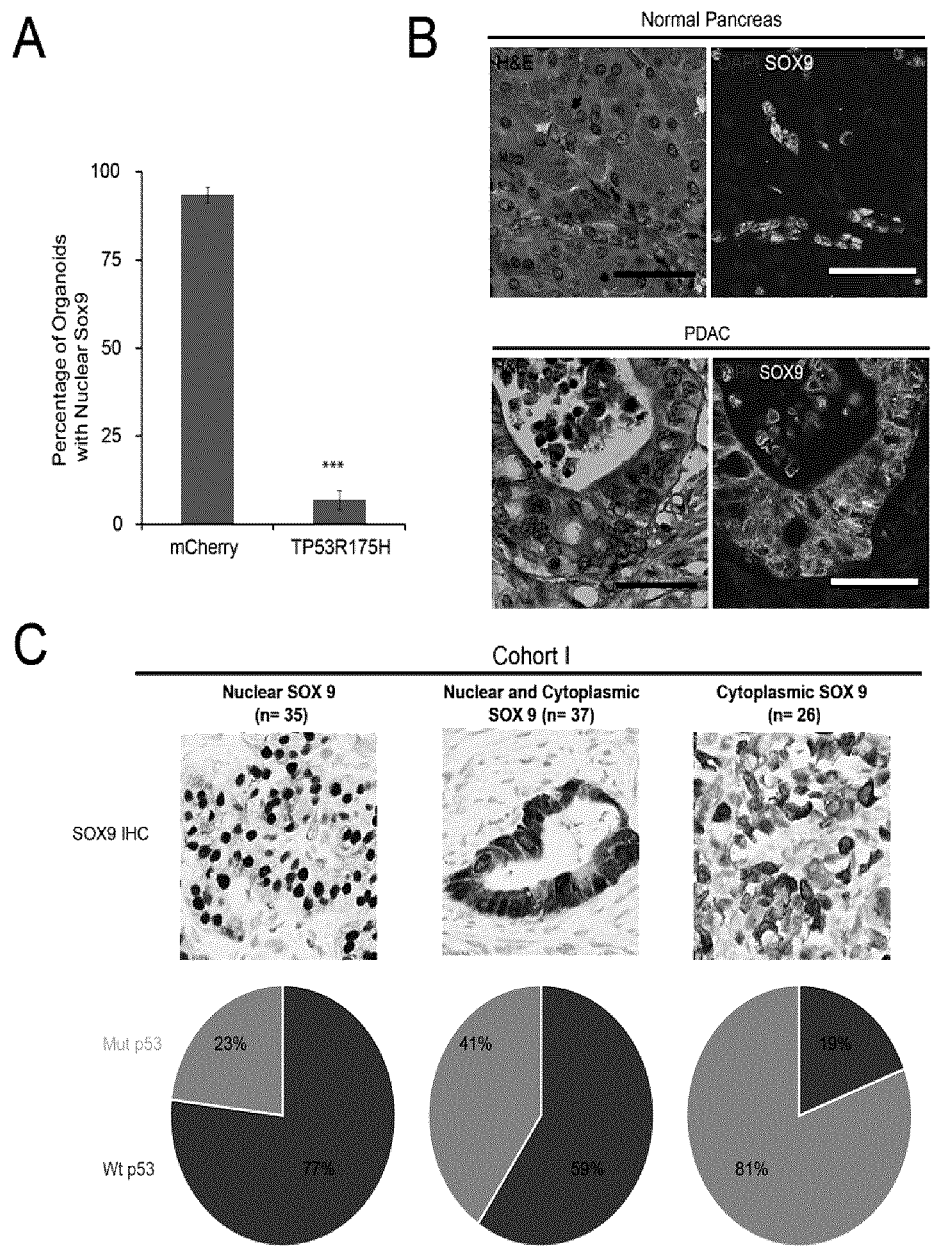
FIG. 5 shows Cytoplasmic SOX9 and Its Relationship to TP53 Status and Clinical Outcome. (A) Quantification for nuclear SOX9 in mCherry-expressing and TP53R175H-expressing pancreatic progenitor-organoids. Graph summarizes results from three independent sets of experiments with over 50 structures counted in each experiment. (B) H&E and immunostaining for SOX9 (bright) in normal pancreas and PDAC. Scale bars, 50 µm. (C) Representative images of chromogenic IHC staining showing nuclear, nuclear-cytoplasmic and cytoplasmic SOX9 staining (top panel). Samples with different SOX9 status scored for TP53 mutation status and expressed as percentage (lower panel). (D) Kaplan-Meir graphs representing disease free survival (DFS) an overall survival (OS) of patients in cohort I with nuclear (n=29), nuclear and cytoplasmic (n=29), or cytoplasmic SOX9 (n=23). (E) Kaplan-Meir graph representing disease specific survival of patients in cohort II with cytoplasmic (n=26) or nuclear SOX9 (n=213).
Figure 5:
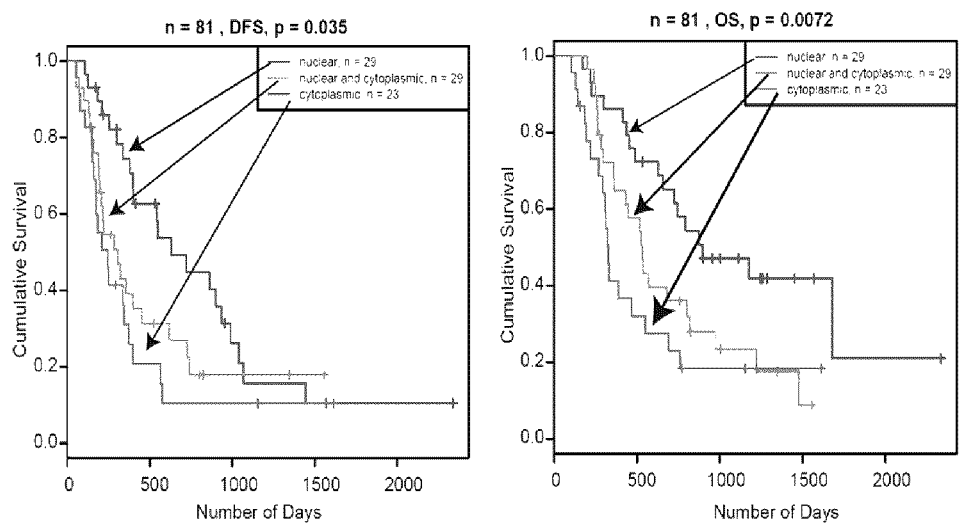
Figure 5:
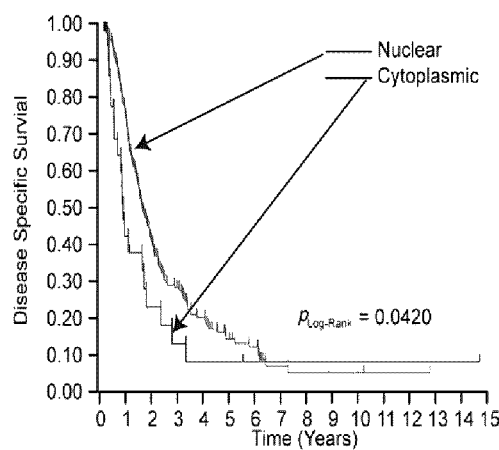

Next, we investigated changes in expression of differentiation state markers in organoids expressing KRASG12V or TP53R175H. Among the markers analyzed, SOX9 showed an unexpected cytoplasmic localization in TP53R175H, but not in mCherry or KRASG12V expressing organoids (FIG. 5A). In breast cancer, cytoplasmic SOX9 is a marker of poor prognosis[21,22]. Driven by this observation, we investigated SOX9 localization in both normal pancreas and PDAC. Normal pancreas (n=4) had nuclear SOX9, whereas PDAC positive for TP53 had cytoplasmic SOX9 (FIG. 5B). To understand the clinical relevance of this observation, we analyzed two independent cohorts of PDAC samples (total n=342) for localization of SOX9 and its relationship to TP53 status. Patients who underwent curative surgical resection of histologically confirmed pancreatic adenocarcinoma and provided consent to tissue and molecular research were included in the studies. Patients were excluded if they had been lost to follow-up or died within 90 days of their surgical resection. Among the PDAC samples with nuclear SOX9, more than 75% had wtTP53 status, whereas, more than 80% of PDAC samples with cytoplasmic SOX9 had mutant TP53 status demonstrating a significant relationship between TP53 status and SOX9 localization ($p=3.25\times10^{-5}$) (FIG. 5C). In addition, in cohort I, the increase of SOX9 cytoplasmic localization was significantly associated with poor disease-free survival (DFS) and overall survival (OS) (p=0.035 for DFS, p=0.0072 for OS) (FIG. 5D). In cohort II, cytoplasmic SOX9 was positively associated with higher tumor grade (p=0.0485) and worse disease-specific survival compared to patients with nuclear SOX9 (p=0.0420) (FIG. 5E). Thus, we demonstrate the utility of progenitor-organoids as an interrogation platform to gain clinically relevant insights into cancer phenotypes regulated by the mutations associated with PDAC.

Establishment of Tumor-Organoids that Conserve Differentiation Status and Histological Organization and Heterogeneity As PDAC originates from the exocrine lineage, we reasoned that our culture conditions may be adapted for growing primary pancreatic tumors. Twenty primary tumor samples obtained directly from surgical resections under institutionally approved research ethics protocols (informed research consent from patient donors) were used to establish organoid cultures. Samples represented 12 females and 8 males and included 17 PDAC, 1 intraductal papillary mucinous neoplasms (IPMN), 1 invasive mucinous cystic neoplasm and 1 acinar cell tumor; isolated from the pancreatic head (n=19) or neck (n=1). PDAC tumors were classified as well (n=1), moderately (n=14), or poorly differentiated (n=3) and ranged in size from 1.0 to 7.0 cm (Table 2). Tumors were enzymatically digested and single cell suspensions plated on Matrigel in PTOM. Organoid cultures were established for 17/20 samples, the three that failed being moderately differentiated or IPMN.

Image analysis of UHN17 organoid culture starting at day one and imaged every 24 hours (FIG. 11A) demonstrated that organoids were often clonally derived. To better understand organoid generation, we performed time-lapse analysis of UHN6 culture every 45 minutes for 10 days (FIG. 6A). Organoids showed dynamic behavior such as structures moving and merging with others, and cells dispersing from an organoid and forming new organoids (data not shown). After 16 days in culture, we analyzed the histoarchitecture and differentiation status of the tumor-organoids. The morphological and cytological features of organoids were strikingly similar to the primary tumors they were derived-from; composed of columnar mucin and non-mucin producing cells growing in irregularly shaped papillary or acinar patterns (FIG. 6B). The tumor-organoids and matched primary tumors had similar differentiation marker expression patterns for KRT19, GATA6, and SOX9 (FIG. 6B and data not shown). None of the tumors or organoids expressed islet (NKX6.1) or acinar (GATA4) cell markers (data not shown).

Figure 11:
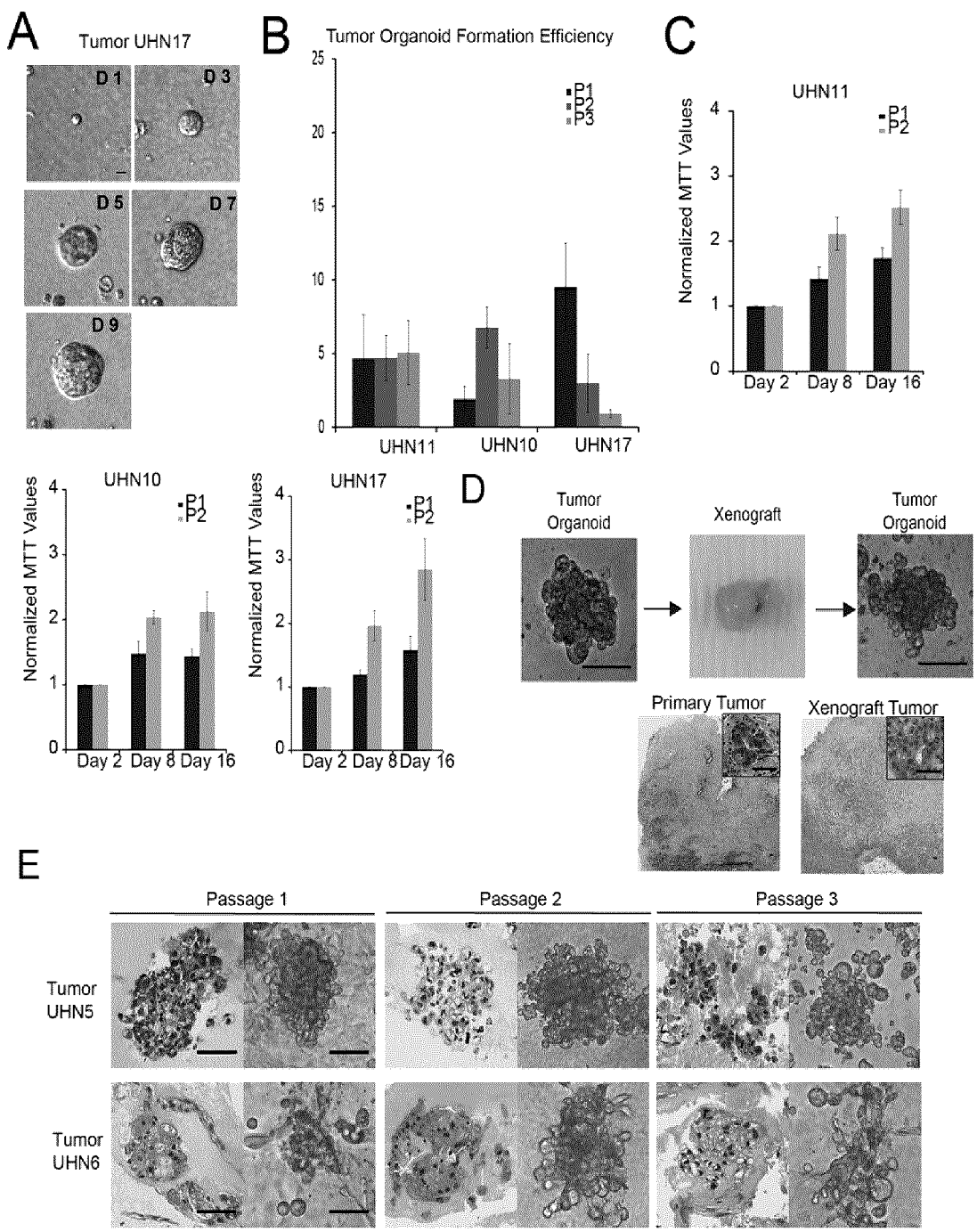
FIG. 11 shows Tumor Organoid Culture from Fresh Resections. (A) Imaging sequence of UHN17 organogenesis. (B) Percent tumor-organoid forming efficiency across three different passages and (C) MTT readings across multiple days for tumor-organoids used in top panel. (D) Propagation of tumor organoids in vivo and in vitro. Day 16 tumor organoids were dissociated and injected subcutanesouly into flanks of NSG mice. Xenograft tumors were observed after 4-7 weeks. Xenograft tumors were then isolated and dissociated to re-seed in 3D. Tumor organoids grew from xenografts showed morphology consistent to original tumor organoids. The lower panel shows the histology of primary tumors from resection (left) and xenograft tumors (right). All scale bars equal to 50 µm. (E) H&E and phase images of tumor-organoids frozen and thawed across multiple passages.

To determine whether the tumor-organoids can be serially passaged and used to generate tumors in vivo, we analyzed organoid forming efficiencies and growth rates of organoids from three PDAC patients. All samples effectively established serial cultures and maintained similar growth rates during the assay period (FIG. 11B). Organoid forming efficiency was dependent on plating density. At low density, 5-10% of the cells formed organoids (FIG. 11B), whereas cells survived and form organoids better when plated at high density. The low organoid forming efficiency of UHN17 in passage three, was an indirect consequence of individual organoids moving and merging to form large structures (FIG. 11B). The organoids can be freeze-thawed to re-establish cultures, which maintain both phase and H&E morphology across passages (FIG. 11E). To test whether the tumor-organoids can generate tumors in xenograft models, we subcutaneously injected 50,000 cells each from two independent organoid cultures (FIG. 11D) into both flanks of NSG mice (n=6 sites per organoid). All injections resulted in tumor growth within 4-7 weeks. The xenograft tumors maintained histoarchitectures present in the primary patient tumors from which the organoids were derived and can be used to re-establish organoids cultures (FIG. 11D).

Carcinomas display intratumoral spatial histological heterogeneity[23], which was maintained in our tumor-organoid system. For example, a primary PDAC that showed two distinct populations of invasive glands, composed of either larger tall columnar cells with cleared granular cytoplasm or smaller cuboidal cells with deeply eosinophilic cytoplasm, generated organoids recapitulating these morphologically distinct populations (FIG. 6C). Thus, we demonstrate that tumor-organoids conserve histological organization, differentiation status, and morphologic heterogeneity observed in primary PDAC. We also show that clonally derived organoids recreate and maintain the histoarchitecture present in the matched primary tumor, over multiple passages and contexts. This cell-autonomous property to regenerate histoarchitecture, which we refer to as "Histopoesis", is likely to be similar to the biology involved in distant metastases that usually resemble the primary tumor and are generated from one or few metastatic cells[24-26].

Tumor-Organoids Retain Patient-Specific Traits and Serve as a Platform for Drug Testing Despite the availability of gemcitabine, gemcitabine+nab-paclitaxel and FOLFIRINOX as first line regimens for treating PDAC, the five year survival rate for patients with PDAC is only six percent[2]. Large-scale genomics studies demonstrate patient-specific variations in genetic and epigenetic changes, highlighting the need to use fresh patient tumor material to evaluate or discover new therapies that can be administered on a personalized basis[27].

Figure 6:
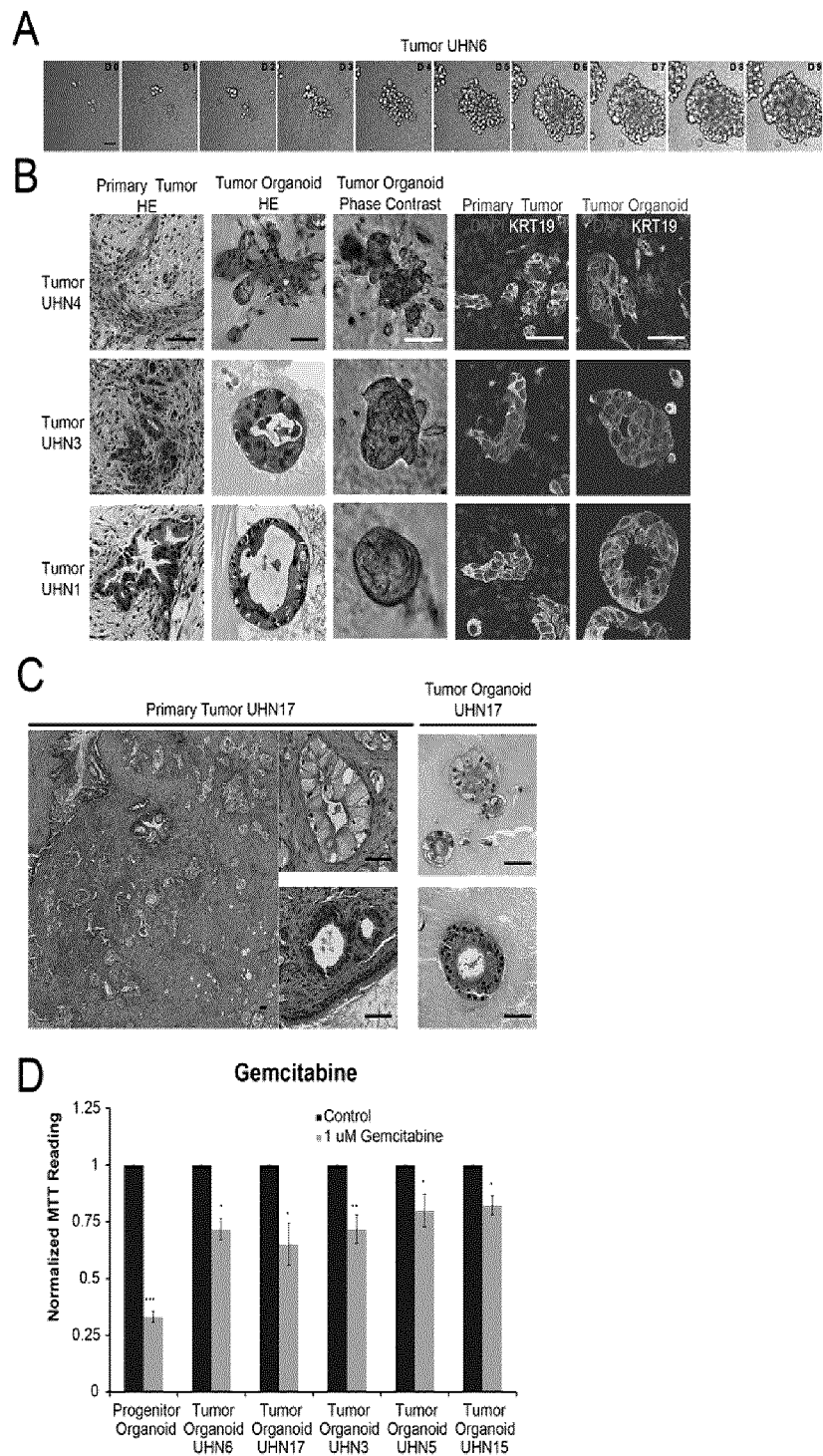
FIG. 6 shows Establishment of Tumor-organoids that Conserve Patient Specific Traits. (A) Time lapse imaging sequence of UHN6 derived organoids. (B) H&E, phase and immunofluorescence images for KRT19 (bright) and DAPI (dark) of images of tumor-organoids and their matched primary tumors. ((C) H&E images showing maintenance of inter-organoid heterogeneity in histoarchitecture representing variation in primary patient tumor. (D) Normalized MTT assay readings of organoid cultures treated with gemcitabine for 4 days. E) Normalized MTT assay readings of organoid cultures with gemcitabine and epigenetic inhibitor of the H3K27me3 writer EZH2 (UNC1999). (F) Normalized MTT reading of tumor-organoids treated with UNC199 alone. See online Methods for details. (G) Immunostaining for H3K27me3 (bright) in two primary patient tumors (top panel) and corresponding tumor-organoids (bottom panel). (H) Basal 02 consumption as measured by Seahorse™ flux analyzer with and without UNC1999 treatment. For MTT and oxygen consumptions experiments, data represent mean+/−S.D. P value (t-test, two tailed): N.S-, not significant; *-p=0.01-0.05; -p=0.001-0.01; *, p=<0.001 (n=3). All scale bars equal to 50 µm.
Figure 6:
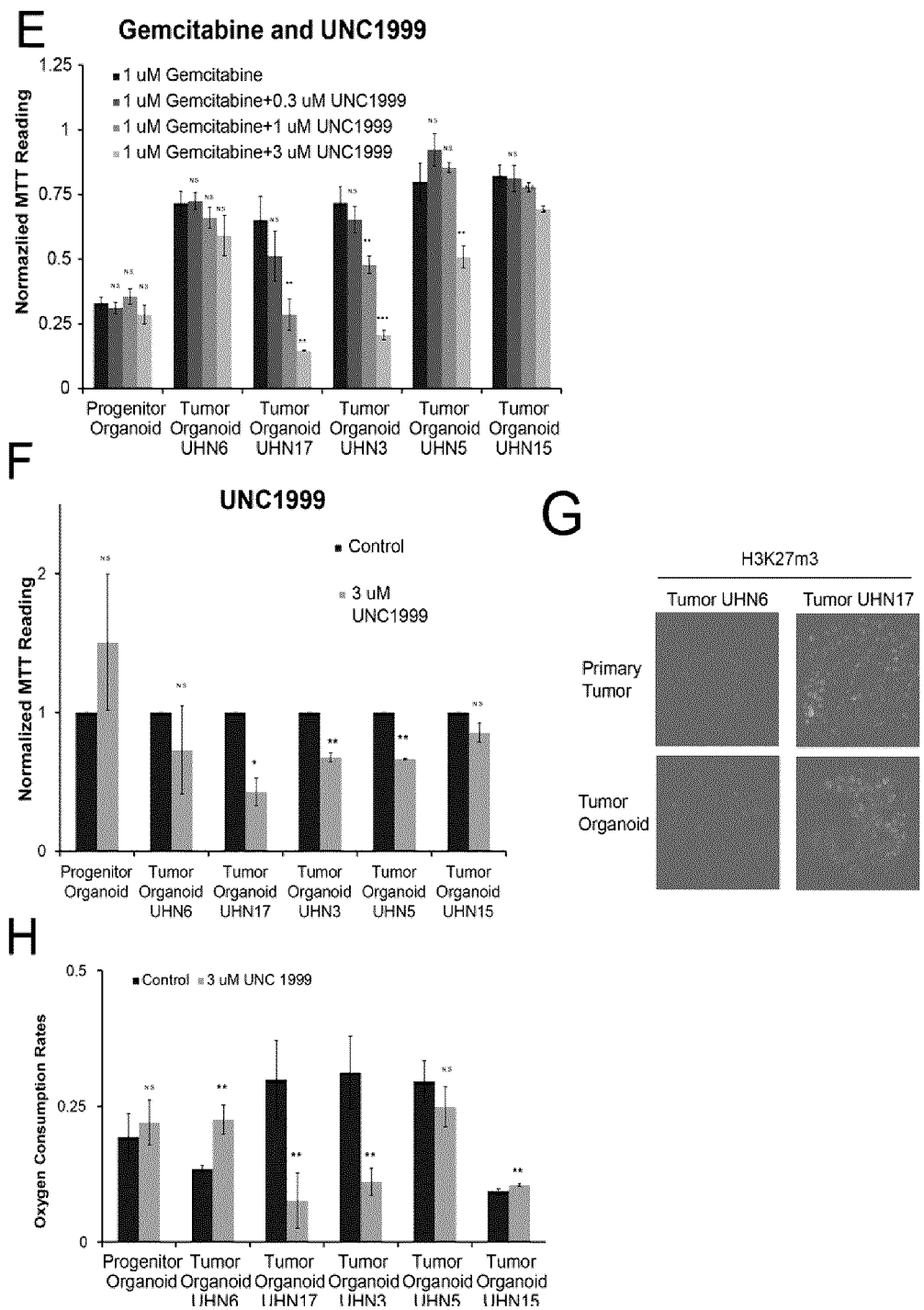
Figure 7:
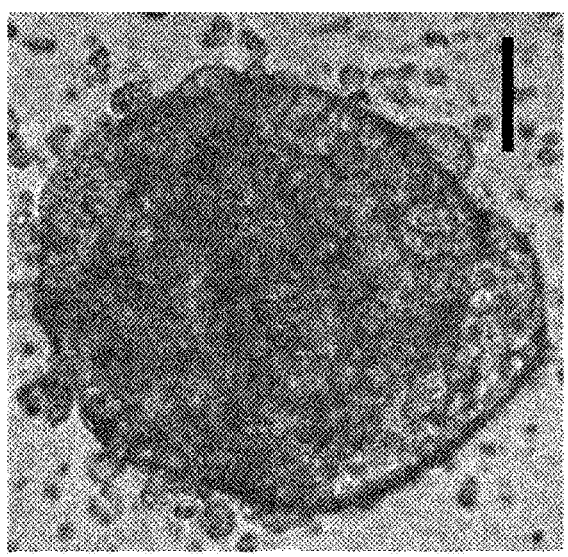
FIG. 7. Shows Establishment of Tumor-organoids from Multiple Types of Tumors. Phase images of lung, prostate and colon tumor organoids derived directly from patients samples. All scale bars equal to 50 µm.
Figure 7:
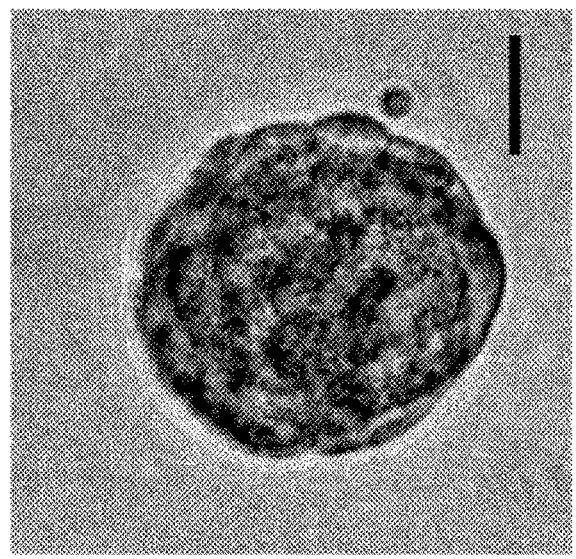
Figure 7:
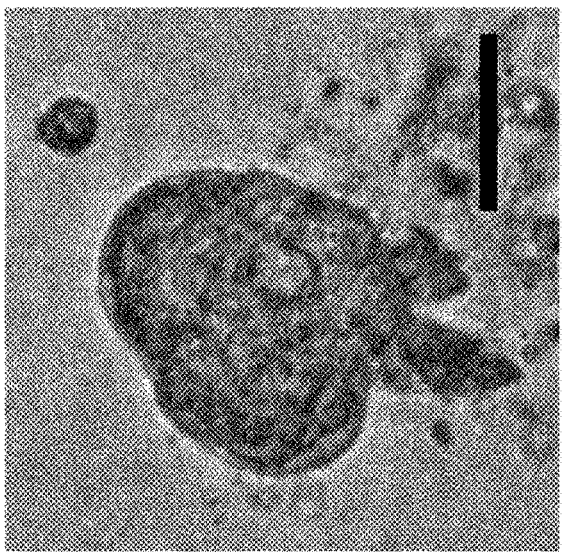
Figure 12:
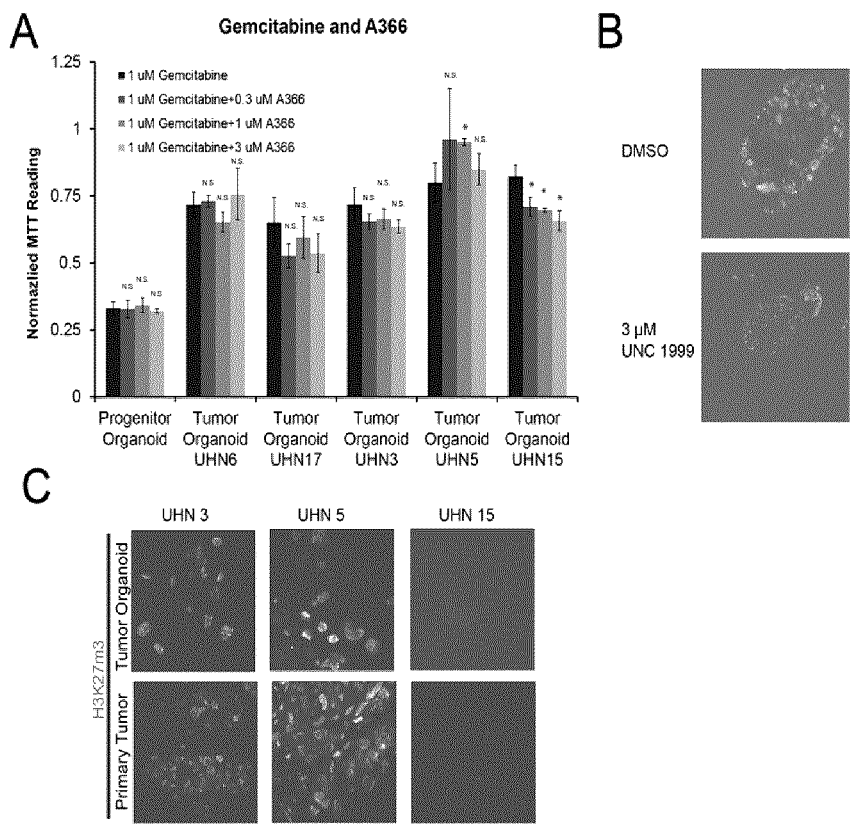
FIG. 12 shows (A) Normalized MTT assay readings of organoid cultures with gemcitabine and epigenetic inhibitors of the H3K9me2 writer G9a (A366). For MTT and oxygen consumptions experiments, data represent mean+/− S.D. P value (t-test, two tailed): N.S-, not significant; *-p=0.01-0.05; -p=0.001-0.01; *, p=<0.001 (n=3). (B) Immunostaining for H3K27me3 in control (DMSO) or UNC 1999-treated tumor-organoids. Scale bars, 50 µm. (C) Tumor-organoids (top panel) and primary tumors (bottom panel) derived from tumor UHN3, UHN 5 and UHN15, show consistent patient-specific variation in staining for H3K27me3. Scale bars, 50 µm.

We analyzed five organoid cultures, UHN6, UHN17, UHN3, UHN5 and UHN15. All cultures show similar poor response to gemcitabine, with 30% growth inhibition in MTT assays (FIG. 6D). As all patients underwent surgery within the past five months and are currently alive with no evidence of disease, we cannot relate organoid response to gemcitabine with patient outcome. We next tested the response of the five tumor-organoid models to drugs targeting epigenetic regulators. These agents were selected due to the lack of treatments targeting mutations frequently observed in PDAC (KRAS, TP53, CDNK2A, and SMAD4). Inhibitors of BET (JQ1), histone deacetylase (LAQ824), DOT1L (SGC0946), G9a (A366) and EZH2 (UNC1999) were tested in progenitor-organoids to investigate their toxicities to normal cells. Inhibitors of G9a (A366), a writer for the H3K9me2 repressive mark, and EZH2 (UNC1999) a writer for the H3K27me3 repressive mark, were least toxic (data not shown) and hence selected for studies in tumor-organoids. A366 and UNC1999 were administered to organoid cultures in combination with the current standard of care, gemcitabine (See FIG. 6 legend and FIG. 12). Organoids were not sensitive to G9a inhibition (FIG. 12A). Whereas, tumor-organoids UHN17, UHN 3, UHN5, and UHN15 but not UHN6, showed dose-dependent decreases in proliferation upon EZH2 inhibition compared to gemcitabine treatment alone (FIG. 6E). EZH2 inhibition alone also was effective in suppressing proliferation of UHN17, UHN3, UHN5 but not UHN6 and UHN15, suggesting EZH2 dependency in the former group (FIG. 6F). Consistent with the differential response to EZH2 inhibition, the matched tumor and organoids of UHN17, UHN3, UHN5 but not UHN6 and UHN15, were positive for H3K27me3 mark (FIG. 6G and data not shown). Treatment with UNC1999 suppressed the H3K27me3 mark in UHN17 organoids at concentrations that exhibited significant growth-inhibitory effects (FIG. 12B).

Recent studies reveal a relationship between oxygenation and regulation of H3K27me3 epigenetic mark[28,29]. Furthermore, cells contributing to tumor relapse in PDAC show increased dependence on oxidative phosphorylation[30]. We measured basal respiration rates to investigate if tumor-organoids show differences in oxygen consumption. The UHN17, UHN3 and UHN5 organoids showed 2-3 fold higher normalized basal oxygen consumption rates compared to UHN6 and UHN15 organoids (FIG. 6H). This increased oxygen consumption was suppressed by EZH2 inhibition in UHN17 and UHN3, suggesting a relationship between epigenetic status and oxygen consumption. In addition, UHN6 and UHN15 organoids and matched tumors, differed in the expression of a known hypoxia marker, GLUT1 (data not shown). Taken together, we demonstrate that tumor-organoids retain patient-specific traits such as repressive epigenetic marks, oxygen consumption and EZH2 dependence, highlighting the utility of this system for identification of precision therapy approaches.

We report conditions for inducing human PSC differentiation to pancreatic exocrine lineage organoids and use these organoids to obtain clinically relevant insights to PDAC. We also adapt the approach for establishing and propagating primary PDAC tumors as organoids that maintain tumor-specific traits, and show differential responses to novel therapeutic drugs.

Previous reports have used mouse pancreas tissue progenitors to develop organoid cultures of ductal cells, which can be manipulated and transplanted in vivo[4-6,31]. We report conditions for differentiation of human PSCs towards exocrine lineage in culture and in vivo. Among the pathways commonly associated with pancreas development, we found inhibition of TGFβ and Notch were required for exocrine differentiation, while Hedgehog inhibition and Wnt activation at stage II and III of induction redirected the developmental program away from the pancreatic lineage (data not shown). Further studies using this model will facilitate a better understanding of exocrine differentiation of human pancreas, which has implications for regenerative medicine.

Progenitor-organoids can also identify cause and effect relationships between early cancer associated alterations and their phenotypes. For example, we report that mutant KRAS or TP53 expression in progenitor-organoids induces mutation-specific phenotypes. In addition, TP53R175H expression, but not KRASG12V, results in cytosolic SOX9 localization. Using two cohorts of human PDAC samples, we validate this finding and identify a correlation between cytosolic SOX9 and mutant TP53 status. Together, these observations demonstrate the power of progenitor-organoids as a platform for understanding genotype-phenotype relationships and obtaining clinically relevant insights for PDAC.

Furthermore, we report culture conditions that support tumor-organoid growth from fresh surgical resections of PDAC with high efficiency (>80%). A recent study reported a method to establish tumor-organoids that have histological features consistent with low-grade PanINs, despite being derived from adenocarcinoma[31]. In contrast, our conditions conserve inter-patient variation in tumor histoarchitecture, and differentiation status between the organoids and the matched primary tumor.

We refer to the ability of single cell derived organoids to recreate both histological characteristics and differentiation status of the tumor as "Histopoesis". As PDAC are stroma rich and our organoids stroma free, histopoesis is likely to be a cell autonomous property of epithelial cells. Several pathology studies have used immunohistochemical analysis to relate primary tumor and metastasis within a patient with ~85% accuracy[24-26]. Since metastases are thought to originate from one or few cells that leave primary tumors, histopoesis can contribute to recreation of histoarchitecture in tumor metastases. It is likely that our organoid system offers a unique opportunity to understand factors that regulate histopoesis.

PDAC organoids have been used for Omics approaches to compare mouse and human tumors to gain new insights[31]. We demonstrate the use of clonally derived organoids to identify sensitivities to novel therapeutic agents in a patient-specific manner. Organoids from different patients showed differential sensitivity to EZH2 inhibition, which correlated with the H3K27me3 mark in both tumor-organoids and matched patient tumor. In addition, the relatively short time required to establish organoid cultures from the time of surgery (21-45 days) minimizes culture-induced genetic drift and is hence likely to better represent the primary tumor than established cell-lines. This is significant because of the implications for using the organoid platform to predict clinical response and designing therapies in a setting of personalized cancer treatment.

Table 1 describes clinical information of patients whose tumor tissues were used in tumor organoid generation.

| Patient IDs | Biobank ICGC Consent | Gender | Age | Incidental Finding | Incidental Finding Details | Other Findings | Pathology Tumor Site | Histological Type | Histological Grade | Tumor Size 1 | Tumor Size 2 |
|---|---|---|---|---|---|---|---|---|---|---|---|
| LHN1 | Y | F | 59 | FALSE | | | Pancreatic Head (C25.0) | Ductal adenocarcinoma | Moderately differentiated | 3.8 | 2.4 |
| LHN2 | Y | F | 75 | FALSE | | | Pancreatic Head (C25.0) | Ductal adenocarcinoma | Moderately differentiated | 3.7 | 3.3 |
| LHN3 | Y | F | 79 | FALSE | | | Pancreatic Head (C25.0) | Ductal adenocarcinoma | Moderately differentiated | 2.4 | 2 |
| LHN4 | Y | F | 60 | FALSE | | | Pancreatic Head (C25.0) | Ductal adenocarcinoma | Moderately differentiated | 2.5 | 2.4 |
| LHN5 | Y | F | 66 | FALSE | | | Pancreatic Head (C25.0) | Ductal adenocarcinoma | Poorly differentiated | 3.2 | 2.6 |
| LHN6 | Y | F | 52 | TRUE | F/U on thyroid cancer | Satiety/ Pain after eating | Pancreatic Head (C25.0) | Ductal adenocarcinoma | Poorly differentiated | 5 | 4.5 |
| LHN7 | Y | F | 77 | TRUE | CT Screening | | Pancreatic Head (C25.0) | Ductal adenocarcinoma | Moderately differentiated | 4 | 3 |
| LHN8 | Y | M | 78 | TRUE | F/U on chronic pancreatic and IPMN | | Pancreatic Head/Body/Tail | IPMN- Intestinal Type, Wan Duct Type | Not specified/ Unknown | 5.8 | 7 |
| LHN9 | Y | F | 67 | FALSE | | | Pancreatic Head (C25.0) | Ductal adenocarcinoma | Moderately differentiated | 2.8 | 2.3 |
| LHN10 | Y | F | 68 | TRUE | Abnormal Liver Functions | | Pancreatic Head (C25.0) | Invasive Mututions Cystic Nioplasm | Well differentiated | 3.8 | 3.7 |
| LHN11 | Y | M | 65 | FALSE | | Ancrenia/ Lethagic | Uncinate Procedd | Ductal adenocarcinoma | Moderately differentiated | 4 | 2 |
| LHN12 | Y | M | 67 | FALSE | | Loose Bowel Movements | Pancreatic Head (C25.0) | Ductal adenocarcinoma | Moderately differentiated | 4.8 | 4.7 |
| LHN13 | Y | F | 62 | FALSE | | Diarrhea | Pancreatic Head & Uncinate Process | Ductal adenocarcinoma | Moderately differentiated | 1.4 | 1 |
| LHN14 | Y | F | 51 | FALSE | | | Pancreatic Head (C25.0) | Ductal adenocarcinoma | Not specified/ Unknown | 3.5 | 2.8 |
| LHN15 | Y | M | 59 | FALSE | | | Pancreatic Head/Uncinate Process/Duodenal Wall/SMV | Ductal adenocarcinoma | Moderately differentiated | 4 | 3.7 |
| LHN16 | Y | M | 76 | FALSE | | | Pancreatic Head (C25.0) | Ductal adenocarcinoma | Moderately differentiated | 3 | 3 |
| LHN17 | Y | F | 46 | FALSE | | | Pancreatic Head & Uncinate Process | Ductal adenocarcinoma | Moderately differentiated | 2.8 | 2.3 |
| LHN18 | Y | M | 69 | TRUE | Annual Physical | | Pancreatic Neck (C25.7) | Ductal adenocarcinoma | Moderately differentiated | 2.1 | 1.8 |

| Patient IDs | | | Age | | | | | | | |
|---|---|---|---|---|---|---|---|---|---|---|
| LHN19 | Y | M | 58 | FALSE | | Pancreatic Head (C25.0) | Ductal adenocarcinoma | Moderately differentiated | 4.4 | 3 |
| LHN20 | Y | M | 63 | FALSE | Change in stool (NOS) | Pancreatic Head (C25.0) | Favor Acirar Cell | Poorly differentiated | 3 | 2.7 |

| Patient IDs | Tumor Size 3 | Invasion Type 1 | Invasion Type 2 | Invasion Type 3 | Invasion Type 4 | Invasion Type 5 | Margins | Revised Margin Submitted |
|---|---|---|---|---|---|---|---|---|
| LHN1 | 2.1 | Lymphatic/vascular Invasion | Perineural Invasion | extra pancreatic exterior | | | Involved | NO |
| LHN2 | 2.8 | No Invasion Found | | | | | Uninvolved | NO |
| LHN3 | 1.3 | common bite duct Invasion | Lymphatic/vascular Invasion | Perineural Invasion | | | Uninvolved | NO |
| LHN4 | 2 | common bite duct Invasion | coocenal Invasion | extra pancreatic exterior | Lymphatic/vascular Invasion | Perineural Invasion | Uninvolved | NO |
| LHN5 | 2.3 | Lymphatic/vascular Invasion | Perineural Invasion | extra pancreatic exterior | | | Uninvolved | NO |
| LHN6 | 4 | Lymphatic/vascular Invasion | Perineural Invasion | Stomach Invasion | Superior mesanteric vein Invasion | extra pancreatic exterior | Uninvolved | NO |
| LHN7 | 2.4 | ducdenal Invasion | extra pancreatic exterior | Lymphatic/vascular Invasion | Perineural Invasion | | Involved | NO |
| LHN8 | | ducdenal Extansion | | | | | Uninvolved | NO |
| LHN9 | 1.8 | Perineural Invasion | Lymphatic/vascular Invasion | comman bite duct Invasion | extra pancreatic extension | | Uninvolved | NO |
| LHN10 | 3.2 | Perineural Invasion | Lymphatic/vascular Invasion | extra pancreatic extension | ducdenal Invasion | | Involved | NO |
| LHN11 | 3 | superior mesanteric vein Invasion | coocenal Invasion | extra pancreatic exterior | Lymphatic/vascular Invasion Indeterminate | Perineural Invasion | Involved | NO |
| LHN12 | 4.2 | Perineural Invasion | Lymphatic/vascular Invasion | ducdenal Invasion | | | Uninvolved | NO |
| LHN13 | 0.3 | extra pancreatic extension | Lymphatic/vascular Invasion | Perineural Invasion | comman bite duct Invasion | | Uninvolved | NO |
| LHN14 | 2 | ducdenal Invasion | Perineural Invasion | comman bite duct Invasion | Lymphatic/vascular Invasion | extra pancreatic extension | Uninvolved | NO |
| LHN15 | 1.9 | Ampulla of Vecter or Spincter of Ocdi Invasion | extra pancreatic extension | Lymphatic/vascular Invasion | Perineural Invasion | superior mesanteric vein Invasion | Uninvolved | NO |
| LHN16 | 1.7 | extra pancreatic extension | Lymphatic/vascular Invasion | Ampulla of Vecter or Spincter of Ocdi Invasion | Perineural Invasion | | Uninvolved | NO |
| LHN17 | 2.2 | extra pancreatic extension | Lymphatic/vascular Invasion | Perineural Invasion | | | Involved | NO |
| LHN18 | 1.5 | Lymphatic/vascular Invasion | Perineural Invasion | | | | Uninvolved | NO |
| LHN19 | 3.8 | Perineural Invasion | coocenal Invasion | extra pancreatic extension | | | Uninvolved | NO |
| LHN20 | 2.5 | Perineural Invasion | Lymphatic/vascular Invasion | extra pancreatic extension | | | Uninvolved | NO |

Table 2 comprises two tables showing analysis of SOX9 localizations against clincopathologic parameters and the significance of multivariable disease specific survival for SOX localization in PDACs in cohort

| Analysis of SOX9 Localization against clinicopathologic parameters. | | | | | |
|---|---|---|---|---|---|
| Clinicopathologic Variable | | Nuclear | Cytoplasmic | Negative | N v C Comparison |
| Age - Mean [Median] | | 65.9 [66.4] | 67.7 [65.7] | 63.4 [60.3] | $p_{Kruckal\ Wale}$ = 0.5945 |
| Sex | Male | 113 (52.6%) | 18 (75.0%) | 1 (33.3%) | $p_{Fishers\ Exact}$ = 0.0502 |
| | Female | 102 (47.4%) | 6 (25.0%) | 2 (66.7%) | |
| Pathologic T-Stage | pT1 | 2 (0.9%) | 0 (0%) | 0 (0%) | $p_{Fishers\ Exact}$ = 0.6145 |
| | pT2 | 12 (5.6%) | 0 (0%) | 0 (0%) | |
| | pT3 | 198 (93.0%) | 23 (100%) | 3 (100%) | |
| | pT4 | 1 (0.5%) | 0 (0%) | 0 (0%) | |

-continued

Analysis of SOX9 Localization against clinicopathologic parameters.

| Clinicopathologic Variable | | Nuclear | Cytoplasmic | Negative | N v C Comparison |
|---|---|---|---|---|---|
| Lymphovascular Invasion | Pos | 115 (53.7%) | 17 (73.9%) | 2 (66.7%) | $p_{Fishers\ Exact}$ = 0.0781 |
|  | Neg | 99 (46.3%) | 6 (26.1%) | 1 (33.3%) |  |
| Perineural Invasion | Pos | 195 (91.6%) | 21 (91.3%) | 3 (100%) | $p_{Fishers\ Exact}$ = 1.0000 |
|  | Neg | 18 (8.4%) | 2 (8.7%) | 0 (0%) |  |
| Regional Lymph Node Status | pN0 | 56 (26.3%) | 3 (13.0%) | 1 (33.3%) | $p_{Fishers\ Exact}$ = 0.2083† |
|  | pN1 | 154 (72.3%) | 20 (87.0%) | 2 (66.7%) |  |
|  | pNX | 3 (1.4%) | 0 (0%) | 0 (0%) |  |
| Adjuvant Chemotherapy | Yes | 68 (32.2%) | 4 (16.7%) | 0 (0%) | $p_{Fishers\ Exact}$ = 0.1607 |
|  | No | 143 (67.8%) | 20 (83.3%) | 3 (100%) |  |
| Tumor Grade | 1 | 3 (1.4%) | 0 (0%) | 0 (0%) | $p_{Fishers\ Exact}$ = 0.0433‡ |
|  | 2 | 162 (75.7%) | 13 (56.5%) | 2 (66.7%) |  |
|  | 3 | 49 (22.9%) | 10 (43.5%) | 1 (33.3%) |  |

Each analyses used all availabe data so the total number of cases evaluated may differ across clinicopathologic variables.
†The 3 cases with pNX recorded for regional lymph node status were excluded in this analysis.
‡The 3 cases with Grade 1 disease were excluded in this analysis.

Multivariable Disease Specific Survival For SOX9 Localization in PDAC

| Clinicopathologic Covariates | Levels | Risk Ratio | 95% CI | p-value |
|---|---|---|---|---|
| Age at Surgery | Entire range of regressor | 1.86 | 0.80-4.34 | 0.1494 |
| Sex | Male v Female | 1.09 | 0.79-1.51 | 0.5935 |
| Adjuvant Chemotherapy | Treated v Untreated | 0.50 | 0.34-0.72 | 0.0002 |
| Lymphovascular Invasion | Present v Absent | 1.28 | 0.91-1.83 | 0.1597 |
| Perineural Invasion | Present v Absent | 1.89 | 0.97-4.17 | 0.0629 |
| pT-Stage | pT4 v pT3 | 0.37 | 0.02-1.80 | 0.7028 |
|  | pT4 v pT2 | 0.34 | 0.02-2.01 |  |
|  | pT4 v pT1 | 0.30 | 0.01-3.28 |  |
|  | pT3 v pT2 | 0.91 | 0.45-2.10 |  |
|  | pT3 v pT1 | 0.79 | 0.24-4.91 |  |
|  | pT2 v pT1 | 0.87 | 0.21-5.87 |  |
| Regional Lymph Nodes pN-Stage | pN1 v pN0 | 2.23 | 1.47-3.45 | <0.0001 |
| Tumor Grade | 3 v 2 | 1.55 | 1.07-2.22 | 0.0417 |
|  | 3 v 1 | 3.54 | 0.73-63.89 |  |
|  | 2 v 1 | 2.28 | 0.48-40.91 |  |
| SOX9 Localization | Cytoplasmic v Nuclear | 1.07 | 0.62-1.75 | 0.8120 |

SOX9 Localization is not an independently prognostic marker due in part to its association with Tumor Grade and Lymphovascular Invasion.

Although preferred embodiments of the invention have been described herein, it will be understood by those skilled in the art that variations may be made thereto without departing from the spirit of the invention or the scope of the appended claims. Further more particular limitations described with respect to different embodiments may be combined in any reasonable manner despite not being the combination not being explicitly described within one embodiment. All documents disclosed herein are incorporated by reference.

REFERENCE LIST

1. Ghaneh, P., Costello, E. & Neoptolemos, J. P. Biology and management of pancreatic cancer. *Postgraduate Medical Journal* 84, 478-497 (2008).
2. Kanji, Z.S. & Gallinger, S. Diagnosis and management of pancreatic cancer. *CMAJ: Canadian Medical Association journal=journal de l'Association medicale canadienne* 185, 1219-1226 (2013).
3. Vincent, A., Herman, J., Schulick, R., Hruban, R. H. & Goggins, M. Pancreatic cancer. *Lancet* 378, 607-620 (2011).
4. Agbunag, C., Lee, K.E., Buontempo, S. & Bar-Sagi, D. Pancreatic duct epithelial cell isolation and cultivation in two-dimensional and three-dimensional culture systems. *Methods Enzymol* 407, 703-710 (2006).
5. Huch, M., et al. Unlimited in vitro expansion of adult bi-potent pancreas progenitors through the Lgr5/R-spondin axis. *The EMBO journal* 32, 2708-2721 (2013).
6. Li, X., et al. Oncogenic transformation of diverse gastrointestinal tissues in primary organoid culture. *Nature medicine* 20, 769-777 (2014).
7. Pagliuca, F. W., et al. Generation of functional human pancreatic beta cells in vitro. *Cell* 159, 428-439 (2014).
8. Rezania, A., et al. Reversal of diabetes with insulin-producing cells derived in vitro from human pluripotent stem cells. *Nature biotechnology* 32, 1121-1133 (2014).
9. Schiesser, J. V. & Wells, J.M. Generation of beta cells from human pluripotent stem cells: are we there yet? *Ann N Y Acad Sci* 1311, 124-137 (2014).
10. Jennings, R. E., et al. Development of the human pancreas from foregut to endocrine commitment. *Diabetes* 62, 3514-3522 (2013).
11. Pan, F. C. & Wright, C. Pancreas organogenesis: from bud to plexus to gland. *Dev Dyn* 240, 530-565 (2011).
12. McCracken, K. W. & Wells, J.M. Molecular pathways controlling pancreas induction. *Semin Cell Dev Biol* 23, 656-662 (2012).
13. Hick, A. C., et al. Mechanism of primitive duct formation in the pancreas and submandibular glands: a role for SDF-1. *BMC Dev Biol* 9, 66 (2009).
14. Riedel, M. J., et al. Immunohistochemical characterisation of cells co-producing insulin and glucagon in the developing human pancreas. *Diabetologia* 55, 372-381 (2012).
15. Lyttle, B. M., et al. Transcription factor expression in the developing human fetal endocrine pancreas. *Diabetologia* 51, 1169-1180 (2008).
16. Outzen, H. C. & Leiter, E. H. Transplantation of pancreatic islets into cleared mammary fat pads. *Transplantation* 32, 101-105 (1981).
17. Laitio, M., Lev, R. & Orlic, D. The developing human fetal pancreas: an ultrastructural and histochemical study with special reference to exocrine cells. *Journal of anatomy* 117, 619-634 (1974).
18. Nielsen, S. K., et al. Characterization of primary cilia and Hedgehog signaling during development of the human pancreas and in human pancreatic duct cancer cell lines. *Dev Dyn* 237, 2039-2052 (2008).
19. Kolodecik, T., Shugrue, C., Ashat, M. & Thrower, E. C. Risk factors for pancreatic cancer: underlying mechanisms and potential targets. *Front Physiol* 4, 415 (2013).
20. Chang, D. K., Grimmond, S.M. & Biankin, A. V. Pancreatic cancer genomics. *Current opinion in genetics & development* 24, 74-81 (2014).
21. Chakravarty, G., Rider, B. & Mondal, D. Cytoplasmic compartmentalization of SOX9 abrogates the growth arrest response of breast cancer cells that can be rescued by trichostatin A treatment. *Cancer Biol Ther* 11, 71-83 (2011).
22. Chakravarty, G., et al. Prognostic significance of cytoplasmic SOX9 in invasive ductal carcinoma and metastatic breast cancer. *Exp Biol Med (Maywood)* 236, 145-155 (2011).
23. Marusyk, A., Almendro, V. & Polyak, K. Intra-tumour heterogeneity: a looking glass for cancer? Nature reviews. *Cancer* 12, 323-334 (2012).
24. Lagendijk, J. H., Mullink, H., van Diest, P. J., Meijer, G. A. & Meijer, C. J. Immunohistochemical differentiation between primary adenocarcinomas of the ovary and ovarian metastases of colonic and breast origin. Comparison between a statistical and an intuitive approach. *Journal of clinical pathology* 52, 283-290 (1999).
25. Dennis, J. L., et al. Markers of adenocarcinoma characteristic of the site of origin: development of a diagnostic algorithm. *Clinical cancer research: an official journal of the American Association for Cancer Research* 11, 3766-3772 (2005).
26. Anderson, G. G. & Weiss, L.M. Determining tissue of origin for metastatic cancers: meta-analysis and literature review of immunohistochemistry performance. *Applied immunohistochemistry & molecular morphology: AIMM/ official publication of the Society for Applied Immunohistochemistry* 18, 3-8 (2010).
27. Waddell, N., et al. Whole genomes redefine the mutational landscape of pancreatic cancer. *Nature* 518, 495-501 (2015).
28. van den Beucken, T., et al. Hypoxia promotes stem cell phenotypes and poor prognosis through epigenetic regulation of DICER. *Nature communications* 5, 5203 (2014).
29. Johnson, A. B., Denko, N. & Barton, M. C. Hypoxia induces a novel signature of chromatin modifications and global repression of transcription. *Mutation research* 640, 174-179 (2008).
30. Viale, A., et al. Oncogene ablation-resistant pancreatic cancer cells depend on mitochondrial function. *Nature* 514, 628-632 (2014).
31. Boj, S. F., et al. Organoid models of human and mouse ductal pancreatic cancer. *Cell* 160, 324-338 (2015).
32. Xiang, B. & Muthuswamy, S. K. Using three-dimensional acinar structures for molecular and cell biological assays. *Methods Enzymol* 406, 692-701 (2006).

The invention claimed is:

1. A method for generating human pancreatic exocrine lineage organoids from pluripotent stem cell-derived pancreatic lineage committed progenitors, comprising:
   a) digesting the pancreatic progenitors isolated from a sample;
   b) plating the progenitors in a Pancreatic Progenitor and Tumor Organoid Medium (PTOM) comprising:
      a cell culture medium selected from DMEM, F12, L-15, or RPMI, or combinations thereof;
      an antioxidant selected from vitamin A or its derivatives, Resveratrol, Fisetin, or L-Glutathione;
      a serum free supplement;
      an insulin receptor agonist;
      a glucocorticoid;
      an FGFR agonist; and
      one or more of an antibiotic, a retinoic receptor agonist, or an EGFR agonist;
   c) replacing the PTOM with a Pancreatic Organoid Differentiation Media I (PODM I) comprising:
      a cell culture medium selected from DMEM, F12, L-15, or RPMI, or combinations thereof;
      an antioxidant;
      a FGF;
      an EGF;
      a TGF-beta inhibitor; and
   d) replacing the PODM I with a Pancreatic Organoid Differentiation Media II (PODM II) comprising:
      a cell culture medium selected from DMEM, F12, L-15, or RPMI, or combinations thereof;
      an antioxidant;
      a FGF;
      an EGF; and
      a serum free supplement.

2. The method of claim 1, wherein the insulin receptor agonist is insulin, Demethylasterriquinone B1, HNG6A, IGFI, or IGF2.

3. The method of claim 1, wherein the glucocorticoid is Dexamethasone, Fluticasone propionate, Hydrocortisone, or Corticosterone.

4. The method of claim 1, wherein the FGFR agonist is at least one of FGF1, FGF2, FGF3, FGF4, FGF5, FGF6, FGF7, FGF8, FGF9 and FGF10.

5. The method of claim 1, wherein the PTOM further comprises a retinoic receptor agonist, wherein the retinoic receptor agonist is retinoic acid.

6. The method of claim 1, wherein the PTOM further comprises an EGFR agonist and the EGFR agonist is one or more of EGF, HGF, a TGF, a NRG, or Amphiregulin.

7. The method of claim 1, wherein the pancreatic exocrine lineage organoids carry an oncogene.

8. The method of claim 7, wherein the oncogene is exogenously introduced.

9. The method of claim 7, wherein the oncogene is a mutant KRAS, a mutant TP53, a mutant CDNK2A, or a mutant SMAD4.

10. A method for generating tumour organoids from a lung tumor, a colon tumor, a prostrate tumor, or a pancreatic tumor, comprising:
   a) digesting the tumour isolated from a sample;
   b) resuspending tumour cells from the tumour in a Pancreatic Progenitor and Tumor Organoid Medium (PTOM) comprising:
      a cell culture medium selected from DMEM, F12, L-15, or RPMI, or combinations thereof;
      an antioxidant selected from vitamin A or its derivatives, Resveratrol, Fisetin, or L-Glutathione;
      a serum free supplement;
      an insulin receptor agonist;
      a glucocorticoid;
      an FGFR agonist; and
      one or more of an antibiotic, a retinoic receptor agonist, or an EGFR agonist;

c) replacing the PTOM with a Pancreatic Organoid Differentiation Media I (PODM I) comprising:
   a cell culture medium selected from DMEM, F12, L-15, or RPMI, or combinations thereof;
   an antioxidant;
   a FGF;
   an EGF; and
   a TGF-beta inhibitor; and
d) replacing the PODM I with a Pancreatic Organoid Differentiation Media II (PODM II) comprising:
   a cell culture medium selected from DMEM, F12, L-15, or RPMI, or combinations thereof;
   an antioxidant;
   a FGF;
   an EGF; and
   a serum free supplement;
wherein the tumor-organoids show similar marker expression patterns with the matched primary tumors.

11. The method of claim 10, wherein the tumour organoids can be maintained for up to 1 year.

12. The method of claim 10, wherein the insulin receptor agonist is insulin, Demethylasterriquinone B 1, HNG6A, IGFI, or IGF2.

13. The method of claim 10, wherein the glucocorticoid is Dexamethasone, Fluticasone propionate, Hydrocortisone, or Corticosterone.

14. The method of claim 10, wherein the FGFR agonist is at least one of FGF1, FGF2, FGF3, FGF4, FGF5, FGF6, FGF7, FGF8, FGF9 and FGF10.

15. The method of claim 10, wherein the retinoic receptor agonist is retinoic acid.

16. The method of claim 10, wherein the EGFR agonist is one or more of EGF, HGF, a TGF, a NRG, or Amphiregulin.

17. The method of claim 10, wherein the resuspending is performed along with a biomatrix substance.

18. The method of claim 10, wherein the plating is performed on a same or different biomatrix substance.

* * * * *